(12) United States Patent
Slassi et al.

(10) Patent No.: US 6,562,809 B1
(45) Date of Patent: May 13, 2003

(54) 3-BICYCLOINDOLE COMPOUNDS

(75) Inventors: Abdelmalik Slassi, Mississauga (CA); Tao Xin, North York (CA); Louise Edwards, Mississauga (CA); Ashok Tehim, Mississauga (CA)

(73) Assignee: NPS Allelix Corp., Mississauga (CA)

( * ) Notice: Subject to any disclaimer, the term of this patent is extended or adjusted under 35 U.S.C. 154(b) by 0 days.

(21) Appl. No.: 09/156,496

(22) Filed: Sep. 18, 1998

(51) Int. Cl.⁷ .................. A61K 31/55; A61K 31/495; A61K 31/44; A61D 25/06; C07D 455/02
(52) U.S. Cl. ................ 514/214.01; 514/214.02; 514/249; 514/299; 514/306; 540/579; 540/593; 544/349; 546/112; 546/138; 546/183
(58) Field of Search .................. 514/249, 299, 514/306, 214.01, 214.02; 540/593, 579; 544/349; 546/112, 138, 183

(56) References Cited

U.S. PATENT DOCUMENTS 5,874,427 A * 2/1999 Filla et al. .................. 514/214
6,251,893 B1 * 6/2001 Maddaford et al. ..... 514/214.01

FOREIGN PATENT DOCUMENTS

| WO | WO 97/11949 | * | 4/1997 |
| WO | WO 97/28162 | * | 8/1997 |

OTHER PUBLICATIONS

Rehse, K. et al. Arch. Pharm. 1994, 327, 67–75.
Repke, D.B. et al J. Org. Chem. 1994, 59,2164–2171.
Rehse, K. et al, Arch. Pharm. 1987, 320, 1072–1083.
King, F.D. J. Chem. Soc. Perkin Trans. I, 1986, 447–453.
Royer, J. et al., Nouveau Journal de Chimie, 1981, 5, 581–585.
Freter, K. J. Org. Chem. 1975, 40, 2525–2529.

* cited by examiner

*Primary Examiner*—Brenda Coleman
(74) *Attorney, Agent, or Firm*—Rothwell, Figg, Ernst & Manbeck

(57) ABSTRACT

Described herein are compounds selective for a 5-HT1D receptor, which have the general formula:

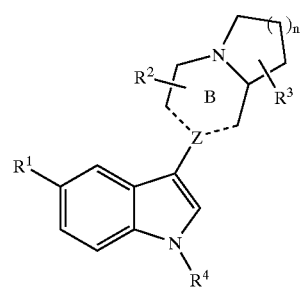

I

19 Claims, No Drawings

3-BICYCLOINDOLE COMPOUNDS

FIELD OF THE INVENTION

This invention relates to 3-bicycloindole compounds, to pharmaceutical and diagnostic compositions containing them and to their medical use, particularly in the treatment or diagnosis of CNS conditions.

BACKGROUND TO THE INVENTION

Through its interaction with receptors borne on neuronal and other cells, 5-hydroxytryptamine (5-HT or serotonin) exerts various physiological effects. Imbalances in this interaction are believed to be responsible for such conditions as anxiety, hallucination, migraine, chemotherapy-induced nausea and for disorders in sexual activity, cardiovascular activity and thermoregulation, among others. From an improved understanding of the 5-HT receptor population, it is apparent that these effects are mediated selectively through individual types and subtypes of the 5-HT receptors. Migraine, for example, has been treated with ergotamine, dihydroergotamine, methylsergide and, most recently, sumatriptan, all of which presumably act at $5\text{-HT}_{1D}$ receptor subtype.

Current treatments for migraine, including sumatriptan, continue to have unwanted side effects. These include coronary vasospasm, hypertension and angina. Recent evidence suggests that sumatriptan's contraction of coronary arteries may be mediated by its stimulation of the $5\text{-HT}_{1B}$ (formerly $5\text{-HT}_{1D\beta}$) subtype of the 5-HT receptors (Kaumann, A. J. Circulation, 1994, 90:1141–1153).

Given the physiological and clinical significance of the $5\text{-HT}_{1D}$ receptor, and the potential side effect liability of stimulation of its $5\text{-HT}_{1B}$ receptor, it would be desirable to provide compounds that bind with high affinity to the $5\text{-HT}_{1D}$ receptor. Such compounds would be medically useful, for example, to treat indications such as migraine and others for which administration of a $5\text{-HT}_{1D}$ ligand is indicated. Also they could be used diagnostically, for example, to identify these receptors and to screen drug candidates.

SUMMARY OF THE INVENTION

According to one aspect of the present invention there are provided compositions, either for use as reagents, for example in the identification of $5\text{-HT}_{1D}$ receptors or receptor ligands, or for pharmaceutical use to treat conditions where stimulation of the $5\text{-HT}_{1D}$ receptor is indicated, containing the compounds of Formula I:

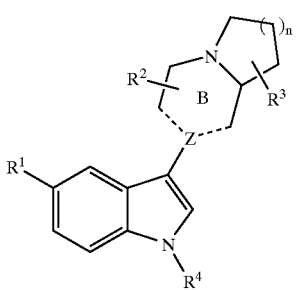

wherein:
$R^1$ is selected from the group consisting of a group of Formula II:

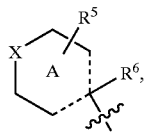

H, halo, OH, $C_{1-6}$alkyl, $C_{1-6}$alkoxy, $C_{2-6}$alkenyl, $C_{2-6}$alkynyl, $C_{3-7}$cycloalkyl, $C_{1-7}$cycloalkenyl, $C_{3-7}$cycloalkoxy, $C_{3-7}$cycloalkylthio, halo-substituted-$C_{1-6}$alkyl, $C_{1-6}$alkylthio, $C_{2-7}$alkanoyl, $C_{2-7}$alkanoyloxy, nitro, cyano, optionally substituted phenyl, optionally substituted furanyl, optionally substituted thienyl, optionally substituted phenyloxy, $CH_2SO_2NR^7R^8$, $C(O)R^9$, $OC(O)R^9$, $NR^{14}R^{15}$, $C(O)NR^{14}R^{15}$, $SO_2NR^{14}R^{15}$, $CO_2R^{16}$, $NHC(O)R^{17}$, $NHC(NR^{16})R^{17}$, $C(NR^{19})NR^{20}R^{21}$, $SCF_3$, $SO_2CF_3$, formyl, $CF_3$ and $CF_3O$;

X is selected from the group consisting of O, S, SO, $SO_2$, $NR^{10}$ and $CR^{11}R^{12}$;

- - - - -, in ring A and ring B, represents a single or double bond provided that only one double bond is present in a ring at a time;

$R^2$ is selected from the group consisting of H, OH, $C_{1-6}$alkyl and $C_{1-6}$alkoxy;

$R^3$ is selected from the group consisting of H, OH, $C_{1-6}$alkyl, $C_{1-6}$alkoxy, $C_{1-6}$alkylthio and optionally substituted benzyloxy;

$R^4$ is selected from the group consisting of H and $C_{1-4}$alkyl;

$R^5$ is selected from the group consisting of H, OH, $C_{1-6}$alkyl and $C_{1-6}$alkoxy;

$R^6$ is selected from the group consisting of H, OH, $C_{1-6}$alkoxy or null, provided that when $R^6$ is selected from the group consisting of H, OH and $C_{1-6}$alkoxy, - - - - - represents a single bond in ring A and when $R^6$ is null, - - - - - represents a double bond in ring A;

$R^7$ and $R^8$ are independently selected from the group consisting of H and $C_{1-6}$alkyl;

$R^9$ is selected from the group consisting of optionally substituted phenyl, optionally substituted pyridyl, optionally substituted thienyl, optionally substituted furanyl and optionally substituted naphthyl;

$R^{10}$ is selected from the group consisting of H, $C_{1-6}$alkyl, optionally substituted benzyl, $C(O)NHR^{13}$, $SO_2NHR^{13}$ and $C(S)NHR^{13}$;

One of $R^{11}$ and $R^{12}$ is selected from the group consisting of H, $C_{1-6}$alkyl and optionally substituted benzyl and the other is H;

$R^{13}$ is selected from the group consisting of H, $C_{1-6}$alkyl, optionally substituted phenyl, optionally substituted benzyl and optionally substituted naphthyl;

$R^{14}$, $R^{15}$ and $R^{16}$ are independently selected from the group consisting of H, $C_{1-6}$alkyl and phenyl or $R^{14}$ and $R^{15}$ may form an alkylene bridge, $-(CH_2)_n-$, where n=3–6, to form, together with the nitrogen to which they are attached a 4- to 7- membered ring;

$R^{17}$ is selected from the group consisting of H, $C_{1-6}$alkyl, $C_{1-6}$alkoxy, phenyl, phenoxy, $NH_2$, alkylamino, dialkylamino, benzyl and benzyloxy;

$R^{18}$ is selected from the group consisting of H and $C_{1-6}$alkyl;

$R^{19}$ is selected from the group consisting of H and $C_{1-6}$alkyl;

$R^{20}$ and $R^{21}$ are independently selected from the group consisting of H and $C_{1-6}$alkyl or one of $R^{20}$ and $R^{21}$, together with $R^{19}$, forms an alkylene bridge, $-(CH_2)_n-$, where n=2 or 3, connecting the nitrogen atoms to which they are attached;

n is selected from the group consisting of an integer of from 1–3; and

Z is selected from the group consisting of C and N, provided that when Z is N, - - - - - represents a single bond in ring B.

It is another aspect of the present invention to provide a method effective to treat medical conditions for which stimulation of the $5\text{-}HT_{1D}$ receptor is indicated, such as to treat migraine.

According to another aspect of the invention, there are provided compounds of Formula III and a salt, solvate or hydrate thereof:

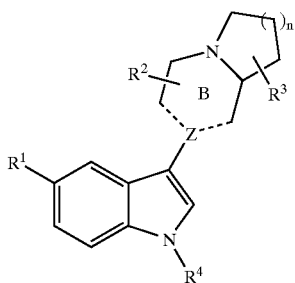

III wherein:
$R^1$ is a group of Formula II:

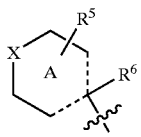

II

X is selected from the group consisting of O, S, SO, $SO_2$, $NR^{10}$ and $CR^{11}R^{12}$;

- - - - -, in ring A and ring B, represents a single or double bond provided that only one double bond is present in a ring at a time;

$R^2$ is selected from the group consisting of H, OH, $C_{1-6}$alkyl and $C_{1-6}$alkoxy;

$R^3$ is selected from the group consisting of H, OH, $C_{1-6}$alkyl, $C_{1-6}$alkoxy, $C_{1-6}$alkylthio and optionally substituted benzyloxy;

$R^4$ is selected from the group consisting of H and $C_{1-4}$alkyl;

$R^5$ is selected from the group consisting of H, OH, $C_{1-6}$alkyl and $C_{1-6}$alkoxy;

$R^6$ is selected from the group consisting of H, OH, $C_{1-6}$alkoxy or null, provided that when $R^6$ is selected from the group consisting of H, OH and $C_{1-6}$alkoxy, - - - - - represents a single bond in ring A and when $R^6$ is null, - - - - - represents a double bond in ring A;

$R^{10}$ is selected from the group consisting of H, $C_{1-6}$alkyl, optionally substituted benzyl, $C(O)NHR^{13}$, $SO_2NHR^{13}$ and $C(S)NHR^{13}$;

One of $R^{11}$ and $R^{12}$ is selected from the group consisting of H, $C_{1-6}$alkyl and optionally substituted benzyl and the other is H;

$R^{13}$ is selected from the group consisting of H, $C_{1-6}$alkyl, optionally substituted phenyl, optionally substituted benzyl and optionally substituted naphthyl;

n is selected from the group consisting of an integer of from 1–3;

Z is selected from the group consisting of C and N, provided that when Z is N, represents a single bond in ring B.

It is an aspect of the present invention to provide a compound that binds to the $5\text{-}HT_{1D}$ receptor.

It is another aspect of the present invention to provide compounds which bind selectively to the $5\text{-}HT_{1D}$ receptor, relative particularly to the $5\text{-}HT_{1B}$ receptor.

These and other aspects of the present invention are described in greater detail hereinbelow.

DETAILED DESCRIPTION AND PREFERRED EMBODIMENTS

The term "$C_{1-6}$alkyl" as used herein means straight and branched chain alkyl radicals containing from one to six carbon atoms and includes methyl, ethyl, propyl, isopropyl, t-butyl and the like.

The term "$C_{1-6}$alkoxy" as used herein means straight and branched chain alkoxy radicals containing from one to six carbon atoms and includes methoxy, ethoxy, propyloxy, isopropyloxy, t-butoxy and the like.

The term "$C_{2-6}$alkenyl" as used herein means straight and branched chain alkenyl radicals containing from two to six carbon atoms and includes ethenyl, 1-propenyl, 1-butenyl and the like.

The term "$C_{2-6}$alkynyl" as used herein means straight and branched chain alkynyl radicals containing from two to six carbon atoms and includes 1-propynyl (propargyl), 1-butynyl and the like.

The term "$C_{3-7}$cycloalkyl" as used herein means saturated carbocyclic radicals containing from 3–7 carbon atoms and includes cyclopropyl, cyclohexyl and the like.

The term "$C_{3-7}$cycoalkyloxy" as used herein means saturated carbocyclo-oxy radicals containing from 3–7 carbon atoms and includes cyclopropyloxy, cyclohexyloxy and the like.

The term "$C_{3-7}$cycloalkylthio" as used herein means saturated carbocycloalkylthio radicals containing from 3–7 carbon atoms and includes cyclopropylthio, cyclohexylthio and the like.

The term "$C_{2-7}$alkanoyl" as used herein means straight and branched chain alkanoyl radicals ($-C(O)C_{1-6}$alkyl) containing from 2–7 atoms and includes acetyl, propionyl, butyryl and the like.

The term "$C_{2-7}$alkanoyloxy" as used herein means straight and branched chain alkanoyloxy radicals ($-OC(O)C_{1-6}$alkyl) containing from 2–7 carbon atoms and includes acetoxy, propionyloxy, butyryloxy and the like.

The term "$C_{4-7}$cycloalkenyl" as used herein means carbocyclic radicals containing from 4–7 carbon atoms and one unit of unsaturation and includes cyclopent-1-enyl, cyclohexenyl and the like.

The term "optionally substituted phenyl" as used herein means an unsubstituted phenyl radical or phenyl radicals substituted with 1–3 substituents independently selected from halo, OH, $C_{1-6}$alkyl, $C_{1-6}$alkoxy, $C_{1-6}$alkylthio, $CF_3$ and $CF_3O$.

The term "optionally substituted phenoxy" as used herein means an unsubstituted phenoxy radical or a phenoxy radical substituted with 1–3 substituents independently selected from halo, OH, $C_{1-6}$alkyl, $C_{1-6}$alkoxy, $C_{1-6}$alkylthio, $CF_3$ and $CF_3O$.

The term "optionally substituted thienyl" as used herein means an unsubstituted thienyl radical or a thienyl radical substituted with 1–2 substituents independently selected from halo, OH, $C_{1-6}$alkyl, $C_{1-6}$alkoxy, $C_{1-6}$alkylthio, $CF_3$ and $CF_3O$.

The term "optionally substituted furanyl" as used herein means an unsubstituted furanyl radical or a furanyl radical substituted with 1–2 substituents independently selected from halo, OH, $C_{1-6}$alkyl, $C_{1-6}$alkoxy, $C_{1-6}$alkylthio, $CF_3$ and $CF_3O$.

The term "optionally substituted pyridyl" as used herein means an unsubstituted pyridyl radical or a pyridyl radical substituted with 1–2 substituents independently selected from halo, OH, $C_{1-6}$alkyl, $C_{1-6}$alkoxy, $C_{1-6}$alkylthio, $CF_3$ and $CF_3O$.

The term "optionally substituted naphthyl" as used herein means an unsubstituted naphthyl radical or a naphthyl radical substituted with 1–4 substituents independently selected from halo, OH, $C_{1-6}$alkyl, $C_{1-6}$alkoxy, $C_{1-4}$alkylthio, $CF_3$ and $CF_3O$.

The term "optionally substituted benzyl" as used herein means an unsubstituted benzyl radical or a benzyl radical substituted on the phenyl ring with 1–3 substituents independently selected from halo, OH, $C_{1-6}$alkyl, $C_{1-6}$alkoxy, $C_{1-6}$alkylthio, $CF_3$ and $CF_3O$.

The term "optionally substituted benzyloxy" as used herein means an unsubstituted benzyloxy radical or a benzyloxy radical substituted on the phenyl ring with 1–3 substituents independently selected from halo, OH, $C_{1-6}$alkyl, $C_{1-6}$alkoxy, $C_{1-6}$alkylthio, $CF_3$ and $CF_3O$.

The term "alkylamino" as used herein means an amino radical which is monosubstituted with a $C_{1-6}$alkyl group.

The term "dialkylamino" as used herein means an amino radical which is disubstituted with $C_{1-6}$alkyl groups, wherein each alkyl group may be the same or different.

The term halo as used herein means halogen and includes fluoro, chloro, bromo, iodo and the like, in both radioactive and non radioactive forms.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formulae I and III or any of their intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of compounds of Formulae I and III are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formulae I and III for laboratory use, or for subsequent conversion to a pharmaceutically acceptable acid addition salt. It should be noted that compounds of Formulae I and III, wherein Z is N, are not stable in the presence of strong acid (for example 1N HCl), therefore when preparing acid addition salts of such compounds, care must be taken to select an appropriately mild acid, for example citric acid.

A "pharmaceutically acceptable basic addition salt" is any non-toxic organic or inorganic base addition salt of the acid compounds represented by Formulae I and III or any of their intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. Those skilled in the art will appreciate that the selection of the appropriate salt may be important so that any ester functionality in the molecule is not hydrolyzed.

"Solvate" means a compound of Formula I or III or the pharmaceutically acceptable salt of a compound of Formula I or III wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general term for all isomers of the individual molecules that differ only in the orientation of their atoms in space. It includes image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The present invention includes within its scope prodrugs of the compounds of Formulae I and III. In general, such prodrugs will be functional derivatives of a compound of Formula I or III which are readily convertible in vivo into the required compound of Formula I or III. Conventional procedures for the selection and preparation of suitable prodrug derivatives are described, for example, in "Design of Prodrugs" ed. H. Bundgaard, Elsevier, 1985.

Compounds of Formula I and III bind selectively (for example with 10-fold selectivity) to the to the serotonin 5-$HT_{1D}$ receptor, relative, particularly, to the serotonin 5-$HT_{1B}$ receptor, as judged by in vitro binding affinities using, for example, the assay exemplified herein. Preferred compounds are those which bind with at least 10-fold selectivity to the 5-HT$_{1D}$ receptor, relative to the 5-HT$_{1B}$ receptor. More preferred compounds are those which bind with at least 40-fold selectivity to the 5-HT$_{1D}$ receptor, relative to the 5-HT$_{1B}$ receptor.

The present invention embodies compositions, either for use as reagents, for example in the identification of 5-HT$_{1D}$ receptors or receptor ligands, or for pharmaceutical use to treat conditions where stimulation of the 5-HT$_{1D}$ receptor is indicated, containing the compounds of Formula I. In further embodiments, the composition comprises a compound of Formula I wherein $R_1$ is selected from a group of Formula II:

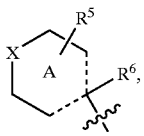

H, halo, OH, $C_{1-6}$alkyl, $C_{1-6}$alkoxy, $C_{2-6}$alkenyl, $C_{2-6}$alkynyl, $C_{3-7}$cycloalkyl, $C_{4-7}$cycloalkenyl, $C_{3-7}$cycloalkoxy, $C_{3-7}$cycloalkylthio, halo-substituted-$C_{1-6}$alkyl, $C_{1-6}$alkylthio, $C_{2-7}$alkanoyl, $C_{2-7}$alkanoyloxy, nitro, cyano, optionally substituted phenyl, optionally substituted furanyl, optionally substituted thienyl, optionally substituted phenyloxy, $CH_2SO_2NR^7R^8$, $C(O)R^9$, $OC(O)R^9$, $NR^{14}R^{15}$, $C(O)NR^{14}R^{15}$, $SO_2NR^{14}R^{15}$, $CO_2R^{16}$, $NHC(O)R^{17}$, $NHC(NR^{18})R^{17}$, $C(NR^{19})NR^{20}R^{21}$, $SCF_3$, $SO_2CF_3$, formyl, $CF_3$ and $CF_3O$. In specific embodiments, $R^1$ is selected from a group of Formula II, H, halo, $C_{1-6}$alkyl, $C_{1-6}$alkoxy, optionally substituted thienyl, optionally substituted furanyl, C(O)Ph, $C_{3-7}$cycloalkoxy, $CF_3$ and $CF_3O$. In more specific embodiments, $R_1$ is selected from a group of Formula II, bromo, fluoro, methyl, isopropyl, methoxy, unsubstituted thienyl, unsubstituted furanyl, C(O)Ph and cyclohexyloxy. In the most specific embodiments, $R_1$ is selected from methyl, isopropyl, unsubstituted thienyl, unsubstituted furanyl and a group of Formula II selected from tetrahydro-2H-pyran-4-ol, cyclohexen-1-yl and 5,6-dihydro-2H-thiopyran-4-yl. When $R^1$ is a group of Formula II, X is selected from O, S, SO, $SO_2$, $NR^{10}$ and $CR^{11}R^{12}$, wherein $R^{10}$ is selected from of H, $C_{1-6}$alkyl, optionally substituted benzyl, $C(O)NHR^{13}$, $SO_2NHR^{13}$ and $C(S)NHR^{13}$ and one of $R^{11}$ and $R^{12}$ is selected from H, $C_{1-6}$alkyl and optionally substituted benzyl and the other is H. In specific embodiments, X is selected from O, S, SO, $SO_2$, $NR^{10}$ and $CR^{11}R^{12}$, wherein $R^{10}$ is selected from H, $C_{1-4}$alkyl and optionally substituted benzyl, and one of $R^{11}$ and $R^{12}$ is selected from H, $C_{1-4}$alkyl and optionally substituted benzyl and the other is H. In more specific embodiments X is selected from O, S, NH, NMethyl, NEthyl, NBenzyl, CHMethyl, CHBenzyl and $CH_2$. Most specifically, X is selected from O, S and $CH_2$. When $R^{10}$ is selected from $C(O)NHR^{13}$, $SO_2NHR^{13}$ and $C(S)NHR^{13}$, $R^{13}$ is selected from the group consisting of H, $C_{1-6}$alkyl, optionally substituted phenyl, optionally substituted benzyl and optionally substituted naphthyl. Specifically, $R^{13}$ is selected from the group consisting of H, $C_{1-4}$alkyl, optionally substituted phenyl and optionally substituted benzyl. More specifically, $R^{13}$ is selected from the group consisting of H, $C_{1-4}$alkyl, unsubstituted phenyl and unsubstituted benzyl. Also within the group of Formula II, $R^5$ is selected from H, OH, $C_{1-6}$alkyl and $C_{1-6}$alkoxy. In specific embodiments, $R^5$ is selected from H, OH, $C_{1-4}$alkyl and $C_{1-4}$alkoxy. In more specific embodiments, $R^5$ is H, OH, methyl and methoxy. In the most specific embodiment, $R^5$ is H. Further, in the group of Formula II, $R^6$ is selected from H, OH, $C_{1-6}$alkoxy or null, provided that when $R_6$ is selected from H, OH and $C_{1-6}$alkoxy, - - - - - represents a single bond in ring A and when $R^6$ is null, - - - - - represents a double bond in ring A. When - - - - - represents a double bond, there is only one double bond present in the ring at a time. In specific embodiments, $R^6$ is selected from H, OH, $C_{1-4}$alkoxy and null. More specifically, $R^6$ is selected from H, OH, methoxy and null. Most specifically, $R^6$ is selected from H and null.

In further embodiments, when the composition comprises a compound of Formula I, wherein $R^1$ is selected from $CH_2SO_2NR^7R^8$, $C(O)R^9$ and $OC(O)R^9$, $R^7$ and $R^8$ are independently selected from the group consisting of H and $C_{1-6}$alkyl and $R^9$ is selected from the group consisting of optionally substituted phenyl, optionally substituted pyridyl, optionally substituted thienyl, optionally substituted furanyl and optionally substituted naphthyl. In specific embodiments, $R^7$ and $R^8$ are independently selected from the group consisting of H and $C_{1-4}$alkyl and $R^9$ is selected from the group consisting of optionally substituted phenyl and optionally substituted naphthyl. More specifically, $R^7$ and $R^8$ are independently selected from the group consisting of H and methyl and $R^9$ is selected from the group consisting of unsubstituted phenyl and unsubstituted naphthyl.

In other embodiments, when the composition comprises a compound of Formula 1, wherein $R^1$ is selected from $NR^{14}R^{15}$, $C(O)NR^{14}R^{15}$, $SO_2NR^{14}R^{15}$, $CH_2SO_2NR^{14}R^{15}$ and $CO_2R^{16}$, $R^{14}$, $R^{15}$ and $R^{16}$ are independently selected from the group consisting of H, $C_{1-6}$alkyl and phenyl or $R^{14}$ and $R^{15}$ may form an alkylene chain, —$(CH_2)_n$—, where n=3–6, to form, together with the nitrogen to which they are attached a 4- to 7-membered ring. In specific embodiments, $R^{14}$, $R^{15}$ and $R^{16}$ are independently selected from the group consisting of H and $C_{1-4}$alkyl or $R^{14}$ and $R^{15}$ may form an alkylene chain, —$(CH_2)_n$—, where n=4–5, to form, together with the nitrogen to which they are attached a 5- to 6-membered ring. In more specific embodiments, $R^{14}$, $R^{15}$ and $R^{16}$ are independently selected from the group consisting of H and methyl or $R^{14}$ and $R^{15}$ may form an alkylene chain, —$(CH_2)_n$—, where n=4–5, to form, together with the nitrogen to which they are attached a 5- to 6-membered ring.

Further embodiments include compositions comprising a compound of Formula I, wherein $R^1$ is selected from NHC(O)$R^{17}$, NHC(NR$^{18}$)$R^{17}$ and $R^{17}$ is selected from H, $C_{1-6}$alkyl, $C_{1-6}$alkoxy, phenyl, phenoxy, $NH_2$, alkylamino, dialkylamino, benzyl and benzyloxy and $R^{18}$ is selected from H and $C_{1-6}$alkyl. In specific embodiments, $R^{17}$ is selected from $C_{1-4}$alkyl, $C_{1-4}$alkoxy, phenyl, phenoxy, $NH_2$, alkylamino, dialkylamino, benzyl and benzyloxy and $R^{18}$ is selected from H and $C_{1-4}$alkyl. In more specific embodiments, $R^{17}$ is selected from methyl, methoxy, phenyl, phenoxy, $NH_2$, alkylamino, dialkylamino, benzyl and benzyloxy and $R^{18}$ is selected from the group consisting of H and methyl. Further, when $R^1$ is $C(NR^{19})NR^{20}R^{21}$ in compounds of Formula I, $R^{19}$ is selected from the group consisting of H and $C_{1-6}$alkyl and $R^{20}$ and $R^{21}$ are independently selected from H and $C_{1-6}$alkyl or one of $R^{20}$ and $R^{21}$, together with $R^{19}$, forms an alkylene chain, —$(CH_2)_n$—, where n=2 or 3, bridging the nitrogen atoms to which they are attached. In specific embodiments, $R^{19}$ is selected from the group consisting of H and $C_{1-4}$alkyl and $R^{20}$ and $R^{21}$ are independently selected from the group consisting of H and $C_{1-4}$alkyl or one of $R^{20}$ and $R^{21}$, together with $R^{19}$, forms an alkylene chain, —$(CH_2)_n$—, where n=2 or 3, bridging the nitrogen atoms to which they are attached. In more specific embodiments, $R^{19}$ is selected from the group consisting of H and methyl and R²⁰ and R²¹ are independently selected from the group consisting of H and methyl or one of R²⁰ and R²¹, together with R¹⁹, forms an alkylene chain, —(CH₂)ₙ—, where n=3, bridging the nitrogen atoms to which they are attached.

In another embodiment of the invention, the composition comprises a compound of Formula I wherein R² is selected from the group consisting of H, OH, C₁₋₆alkyl and C₁₋₆alkoxy and R³ is selected from the group consisting of H, OH, C₁₋₆alkyl, C₁₋₆alkoxy, C₁₋₆alkylthio and optionally substituted benzyloxy. In specific embodiments, R² is selected from the group consisting of H, and C₁₋₄alkyl and R³ is selected from the group consisting of H, C₁₋₄alkyl, C₁₋₄alkoxy and C₁₋₄alkylthio. In more specific embodiments, R² is selected from H and methyl and R³ is H.

In a further embodiment of the invention, the composition comprises a compound of Formula I wherein R⁴ is selected from H and C₁₋₄alkyl. In specific embodiments, R⁴ is H and methyl. In preferred embodiments, R⁴ is H.

In another of its embodiments, the invention includes compositions comprising a compound of Formula I wherein where n is selected from the group consisting of an integer of from 1–3. Specifically, n is selected from 1 and 2. More specifically, n is 1.

In further embodiments of the invention, the composition comprises a compound of Formula I wherein Z is selected from the group consisting of C and N and - - - - - represents a single or double bond, provided that when Z is N, - - - - - represents a single bond in ring B. In preferred embodiments, Z is C and - - - - - represents either a single or double bond in ring B. In more preferred embodiments, - - - - - represents a double bond and (when n is 1) this double bond is located in the 6,7-position of the indolizine ring system.

Specifically, the composition comprises a compound of Formula I selected from:

5-Fluoro-3-[(8a-R,S)-1,2,3,5,8,8a-hexahydro-7-indolizinyl]-1H-indole;
5-Methoxy-3-[(8a-R,S)-1,2,3,5,8,8a-hexahydro-7-indolizinyl]-1H-indole;
5-Methyl-3-[(8a-R,S)-1,2,3,5,8,8a-hexahydro-7-indolizinyl]-1H-indole;
5-Isopropyl-3-[(8a-R,S)-1,2,3,5,8,8a-hexahydro-7-indolizinyl]-1H-indole;
5-Bromo-3-[(8a-R,S)-1,2,3,5,8,8a-hexahydro-7-indolizinyl]-1H-indole;
5-Cyclohexyloxy-3-[(8a-R,S)-1,2,3,5,8,8a-hexahydro-7-indolizinyl]-1H-indole;
5-(2-Thienyl)-3-[(8a-R,S)-1,2,3,5,8,8a-hexahydro-7-indolizinyl]-1H-indole;
5-Isopropyl-3-[(8a,R,S)-6-methyl-1,2,3,5,8,8a-hexahydro-7-indolizinyl]-1H-indole;
1-{[3-(8a-R,S)-1,2,3,5,8,8a-hexahydro-7-indolizinyl]-1H-indol-5-yl}cyclohexanol;
1-{[3-(8a-R,S)-1,2,3,5,8,8a-Hexahydro-7-indolizinyl]-1H-indol-5-yl}-N-methyl-4-azacyclohexanol;
4-{[3-(8a-R,S)-1,2,3,5,8,8a-Hexahydro-7-indolizinyl]-1H-indol-5-yl}tetrahydro-2H-pyran4-ol;
5-(5,6-Dihydro-2H-pyran-4-yl)-3-[(8a-R,S)-1,2,3,5,8,8a-hexahydro-7-indolizinyl]-1H-indole;
5-(5,6-Dihydro-2H-pyran-4-yl)-3-[(8a-R,S)-1,2,3,5,6,8a-hexahydro-7-indolizinyl]-1H-indole;
5-Fluoro-3-[(7R or 7S)(8a-R,S)-octahydro-7-indolizinyl]-1H-indole, Isomer I;
5-Fluoro-3-[(7R or 7S)(8a-R,S)-octahydro-7-indolizinyl]-1H-indole, Isomer II;
5-Isopropyl-3-[(7R or 7S)(8a-R,S)-octahydro-7-indolizinyl]-1H-indole, Isomer I;
5-Isopropyl-3-[(7R or 7S)(8a-R,S)-octahydro-7-indolizinyl]-1H-indole, Isomer II;
5-Methoxy-[(7R or 7S)(8a-R,S)-octahydro-7-indolizinyl]-1H-indole, Isomer I;
5-Methoxy-3-[(7R or 7S)(8a-R,S)-octahydro-7-indolizinyl]-1H-indole, Isomer II;
5-(Tetrahydropyran-4-yl)-[(7-R,S)(8a-R,S)-octahydro-7-indolizinyl]-1H-indole;
5-Bromo-3-[(7-R,S)(8a-R,S)-octahydro-7-indolizinyl]-1H-indole;
3-[(6-R,S)-1,4-Diaza[4.3.0]bicyclonon-4-yl]-1H-indole;
3-[(6-R,S)-1,4-Diaza[4.4.0]bicyclodecan-4-yl]-1H-indole;
5-(Cyclohexen-1-yl)-3-[(8a-R,S)-1,2,3,5,8,8a-hexahydro-7-indolizinyl]-1H-indole;
5-(Cyclohexen-1-yl)-3-[(8a-R,S)-1,2,3,5,6,8a-hexahydro-7-indolizinyl]-1H-indole;
5-(5,6-Dihydro-2H-thiopyran-4-yl)-3-[(8a-R,S)-1,2,3,5,8,8a-hexahydro-7-indolizinyl]-1H-indole;
5-(5,6-Dihydro-2H-thiopyran-4-yl)-3-[(8a-R,S)-1,2,3,5,6,8a-hexahydro-7-indolizinyl]-1H-indole;
3-[(7-R,S)(8a-R,S)-Octahydro-7-indolizinyl]-5-(2-thienyl)-1H-indole; {3-[(7R or 7S)(8a-R,S)-Octahydro-7-indolizinyl]1H-indol-5-yl}phenylmethanone, Isomer I;
{3-[(7R or 7S)(8a-R,S)-Octahydro-7-indolizinyl]1H-indol-5-yl}phenylmethanone, Isomer II; and
{3-[(8a-R,S)-1,2,3,5,8,8a-Hexahydro-7-indolizinyl]-1H-indol-5-yl}phenylmethanone.

In more specific embodiments of the invention, the composition comprises a compound of Formula I selected from:

5-Methoxy-3-[(8a-R,S)-1,2,3,5,8,8a-hexahydro-7-indolizinyl]-1H-indole;
5-Methyl-3-[(8a-R,S)-1,2,3,5,8,8a-hexahydro-7-indolizinyl]-1H-indole;
5-Isopropyl-3-[(8a-R,S)-1,2,3,5,8,8a-hexahydro-7-indolizinyl]-1H-indole;
5-Bromo-3-[(8a-R,S)-1,2,3,5,8,8a-hexahydro-7-indolizinyl]-1H-indole;
5-Cyclohexyloxy-3-[(8a-R,S)-1,2,3,5,8,8a-hexahydro-7-indolizinyl]-1H-indole;
5-(2-Thienyl)-3-[(8a-R,S)-1,2,3,5,8,8a-hexahydro-7-indolizinyl]-1H-indole;
5-Isopropyl-3-[(8a,R,S)-6-methyl-1,2,3,5,8,8a-hexahydro-7-indolizinyl]-1H-indole;
1-{[3-(8a-R,S)-1,2,3,5,8,8a-Hexahydro-7-indolizinyl]-1H-indol-5-yl}cyclohexanol;
4-{[3-(8a-R,S)-1,2,3,5,8,8a-Hexahydro-7-indolizinyl]-1H-indol-5-yl}tetrahydro-2H-pyran-4-ol;
5-(5,6-Dihydro-2H-pyran-4-yl)-3-[(8a-R,S)-1,2,3,5,8,8a-hexahydro-7-indolizinyl]-1H-indole;
5-(5,6-Dihydro-2H-pyran-4-yl)-3-[(8a-R,S)-1,2,3,5,6,8a-hexahydro-7-indolizinyl]-1H-indole;
5-Isopropyl-3-[(7R or 7S)(8a-R,S)-octahydro-7-indolizinyl]-1H-indole, Isomer I;
5-Isopropyl-3-[(7R or 7S)(8a-R,S)-octahydro-7-indolizinyl]-1H-indole, Isomer II;
5-(Tetrahydropyran-4-yl)-[(7-R,S)(8a-R,S)-octahydro-7-indolizinyl]-1H-indole;
5-(Cyclohexen-1-yl)-3-[(8a-R,S)-1,2,3,5,8,8a-hexahydro-7-indolizinyl]-1H-indole;

5-(Cyclohexen-1-yl)-3-[(8a-R,S)-1,2,3,5,6,8a-hexahydro-7-indolizinyl]-1H-indole;

5-(5,6-Dihydro-2H-thiopyran-4-yl)-3-[(8a-R,S)-1,2,3,5,8,8a-hexahydro-7-indolizinyl]-1H-indole;

5-(5,6-Dihydro-2H-thiopyran-4-yl)-3-[(8a-R,S)-1,2,3,5,6,8a-hexahydro-7-indolizinyl]-1H-indole; and 3-[(7-R,S)(8a-R,S)-Octahydro-7-indolizinyl]-5-(2-thienyl)-1H-indole.

In even more specific embodiments of the invention, the composition comprises a compound of Formula I selected from:

5-Methoxy-3-[(8a-R,S)-1,2,3,5,8,8a-hexahydro-7-indolizinyl]-1H-indole;

5-Methyl-3-[(8a-R,S)-1,2,3,5,8,8a-hexahydro-7-indolizinyl]-1H-indole;

5-Isopropyl-3-[(8a-R,S)-1,2,3,5,8,8a-hexahydro-7-indolizinyl]-1H-indole;

5-Isopropyl-3-[(8a,R,S)-6-methyl-1,2,3,5,8,8a-hexahydro-7-indolizinyl]-1H-indole;

1-{[3-(8a-R,S)-1,2,3,5,8,8a-Hexahydro-7-indolizinyl]-1H-indol-5-yl}cyclohexanol;

4-{[3-(8a-R,S)-1,2,3,5,8,8a-Hexahydro-7-indolizinyl]-1H-indol-5-yl}tetrahydro-2H-pyran-4-ol;

5-Isopropyl-3-[(7R or 7S)(8a-R,S)-octahydro-7-indolizinyl]-1H-indole, Isomer I;

5-Isopropyl-3-[(7R or 7S)(8a-R,S)-octahydro-7-indolizinyl]-1H-indole, Isomer II;

5-(Cyclohexen-1-yl)-3-[(8a-R,S)-1,2,3,5,8,8a-hexahydro-7-indolizinyl]-1H-indole;

5-(5,6-Dihydro-2H-thiopyran-4-yl)-3-[(8a-R,S)-1,2,3,5,8,8a-hexahydro-7-indolizinyl]-1H-indole; and 3-[(7-R,S)(8a-R,S)-Octahydro-7-indolizinyl]-5-(2-thienyl)-1H-indole.

In the most specific embodiments of the invention, the composition comprises a compound of Formula I selected from:

5-Methyl-3-[(8a-R,S)-1,2,3,5,8,8a-hexahydro-7-indolizinyl]-1H-indole;

5-isopropyl-3-[(8a-R,S)-1,2,3,5,8,8a-hexahydro-7-indolizinyl]-1H-indole;

5-Isopropyl-3-[(8a,R,S)-6-methyl-1,2,3,5,8,8a-hexahydro-7-indolizinyl]-1H-indole;

5-Isopropyl-3-[(7R or 7S)(8a-R,S)-octahydro-7-indolizinyl]-1H-indole, Isomer II; and 3-[(7-R,S)(8a-R,S)-Octahydro-7-indolizinyl]-5-(2-thienyl)-1H-indole.

The present invention also provides compounds of Formula III. In embodiments of the invention, compounds of Formula III include those in which $R^1$ is a group of Formula II:

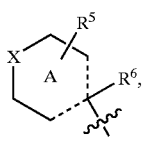

II

Within the group of Formula II, X is selected from O, S, SO, $SO_2$, $NR^{10}$ and $C^{11}R^{12}$, wherein $R^{10}$ is selected from H, $C_{1-6}$alkyl, optionally substituted benzyl, $C(O)NHR^{13}$, $SO_2NHR^{13}$ and $C(S)NHR^{13}$; and one of $R^{11}$ and $R^{12}$ is selected from H, $C_{1-6}$alkyl and optionally substituted benzyl and the other is H. In specific embodiments, X is selected from O, S, SO, $SO_2$, $NR^{10}$ and $CR^{11}R^{12}$, wherein $R^{10}$ is selected from H, $C_{1-4}$alkyl and optionally substituted benzyl, and one of $R^{11}$ and $R^{12}$ is selected from H, $C_{1-4}$alkyl and optionally substituted benzyl and the other is H. In more specific embodiments X is selected from O, S, NH, NMethyl, NEthyl, NBenzyl, CHMethyl, CHBenzyl and $CH_2$. Most specifically, X is selected from O, S and $CH_2$. When $R^{10}$ is selected from $C(O)NHR^{13}$, $SO_2NHR^{13}$ and $C(S)NHR^{13}$, $R^{13}$ is selected from the group consisting of H, $C_{1-6}$alkyl, optionally substituted phenyl, optionally substituted benzyl and optionally substituted naphthyl. Specifically, $R^{13}$ is selected from the group consisting of H, $C_{1-4}$alkyl, optionally substituted phenyl and optionally substituted benzyl. More specifically, $R^{13}$ is selected from the group consisting of H, $C_{1-4}$alkyl, unsubstituted phenyl and unsubstituted benzyl. Also within the group of Formula II, $R^5$ is selected from H, OH, $C_{1-6}$alkyl and $C_{1-6}$alkoxy. In specific embodiments, $R^5$ is selected from H, OH, $C_{1-4}$alkyl and $C_{1-4}$alkoxy. In more specific embodiments, $R^5$ is H, OH, methyl and methoxy. In the most specific embodiment, $R^5$ is H. Further, in the group of Formula II, $R^6$ is selected from H, OH, $C_{1-6}$alkoxy or null, provided that when $R^6$ is selected from H, OH and $C_{1-6}$alkoxy, ----- represents a single bond in ring A and when $R^5$ is null, ----- represents a double bond in ring A. When ----- represents a double bond, there is only one double bond present in the ring at a time. In specific embodiments, $R^6$ is selected from H, OH, $C_{1-4}$alkoxy and null. More specifically, $R^6$ is selected from H, OH, methoxy and null. Most specifically, $R^6$ is selected from H and null.

In further embodiments of the invention, compounds of Formula III include those in which $R^2$ is selected from the group consisting of H, OH, $C_{1-6}$alkyl and $C_{1-6}$alkoxy and $R^3$ is selected from the group consisting of H, OH, $C_{1-6}$alkyl, $C_{1-6}$alkoxy, $C_{1-6}$alkylthio and optionally substituted benzyloxy. In specific embodiments, $R^2$ is selected from the group consisting of H, and $C_{1-4}$alkyl and $R^3$ is selected from the group consisting of H, $C_{1-4}$alkyl, $C_{1-4}$alkoxy and $C_{1-4}$alkylthio. In more specific embodiments, $R^2$ is selected from H and methyl and $R^3$ is H.

In another embodiment of the invention, compounds of Formula III include those in which $R^4$ is selected from H and $C_{1-4}$alkyl. In specific embodiments $R^4$ is selected from H and methyl. In preferred embodiments, $R^4$ is H.

In another of its embodiments, the invention includes compounds of Formula III where n is selected from the group consisting of an integer of from 1–3. Specifically, n is selected from 1 and 2. More specifically, n is 1.

In further embodiments of the invention, compounds of Formula III include those in which Z is selected from the group consisting of C and N and ----- represents a single or double bond, provided that when Z is N, ----- represents a single bond in ring B. In preferred embodiments, Z is C and ----- represents either a single or double bond in ring B. In more preferred embodiments, ----- represents a double bond and (when n is 1) this double bond is located in the 6,7-position of the indolizine ring system.

Specific compounds of Formula III include:

1-{[3-(8a-R,S)-1,2,3,5,8,8a-hexahydro-7-indolizinyl]-1H-indol-5-yl}-N-methyl-4-azacyclohexanol;

4-{[3-(8a-R,S)-1,2,3,5,8,8a-Hexahydro-7-indolizinyl]-1H-indol-5-yl}tetrahydro-2H-pyran-4-ol;

1-{[3-(8a-R,S)-1,2,3,5,8,8a-Hexahydro-7-indolizinyl]-1H-indol-5-yl}cyclohexanol;

5-(5,6-Dihydro-2H-pyran-4-yl)-3-[(8a-R,S)-1,2,3,5,8,8a-hexahydro-7-indolizinyl]-1H-indole;

5-(5,6-Dihydro-2H-pyran-4-yl)-3-[(8a-R,S)-1,2,3,5,6,8a-hexahydro-7-indolizinyl]-1H-indole;

5-(Tetrahydropyran-4-yl)-[(7-R,S)(8a-R,S)-octahydro-7-indolizinyl]-1H-indole;

5-(Cyclohexen-1-yl)-3-[(8a-R,S)-1,2,3,5,8,8a-hexahydro-7-indolizinyl]-1H-indole;

5-(Cyclohexen-1-yl)-3-[(8a-R,S)-1,2,3,5,6,8a-hexahydro-7-indolizinyl]-1H-indole;

5-(5,6-Dihydro-2H-thiopyran-4-yl)-3-[(8a-R,S)-1,2,3,5,8,8a-hexahydro-7-indolizinyl]-1H-indole;

5-(5,6-Dihydro-2H-thiopyran-4-yl)-3-[(8a-R,S)-1,2,3,5,6,8a-hexahydro-7-indolizinyl]-1H-indole; and {3-[(8a-R,S)-1,2,3,5,8,8a-Hexahydro-7-indolizinyl]-1H-indol-5-yl}phenylmethanone.

In more specific embodiments of the invention, the compounds of Formula III include:

4-{[3-(8a-R,S)-1,2,3,5,8,8a-Hexahydro-7-indolizinyl]-1H-indol-5-yl}tetrahydro-2H-pyran-4-ol;

1-{[3-(8a-R,S)-1,2,3,5,8,8a-Hexahydro-7-indolizinyl]-1H-indol-5-yl}cyclohexanol;

5-(5,6-Dihydro-2H-pyran-4-yl)-3-[(8a-R,S)-1,2,3,5,8,8a-hexahydro-7-indolizinyl]-1H-indole;

5-(5,6-Dihydro-2H-pyran-4-yl)-3-[(8a-R,S)-1,2,3,5,6,8a-hexahydro-7-indolizinyl]-1H-indole;

5-(Cyclohexen-1-yl)-3-[(8a-R,S)-1,2,3,5,8,8a-hexahydro-7-indolizinyl]-1H-indole; and 5-(5,6-Dihydro-2H-thiopyran-4-yl)-3-[(8a-R,S)-1,2,3,5,8,8a-hexahydro-7-indolizinyl]-1H-indole.

In even more specific embodiments of the invention, the compounds of Formula III include:

4-{[3-(8a-R,S)-1,2,3,5,8,8a-Hexahydro-7-indolizinyl]-1H-indol-5-yl}tetrahydro-2H-pyran-4-ol;

5-(Cyclohexen-1-yl)-3-[(8a-R,S)-1,2,3,5,8,8a-hexahydro-7-indolizinyl]-1H-indole; and 5-(5,6-Dihydro-2H-thiopyran-4-yl)-3-[(8a-R,S)-1,2,3,5,8,8a-hexahydro-7-indolizinyl]-1H-indole.

All of the compounds of Formulae I and III have at least one asymmetric centre. Where the compounds according to the invention have one asymmetric centre they may exist as enantiomers. Where the compounds according to the invention possess two or more asymmetric centres, they may additionally exist as diastereomers. It is to be understood that all such isomers and mixtures thereof in any proportion are encompassed within the scope of the present invention.

Acid addition salts of the compounds of Formulae I and III are most suitably formed from pharmaceutically acceptable acids, and include for example those formed with inorganic acids e.g. hydrochloric, sulphuric or phosphoric acids (not recommended when Z=N) and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt.

The conversion of a given compound salt to a desired compound salt is achieved by applying standard techniques in which an aqueous solution of the given salt is treated with a solution of base or acid, e.g. sodium carbonate, potassium hydroxide or hydrochloric acid (provided that caution is taken when Z is N) or, to liberate the neutral compound which is then extracted into an appropriate solvent, such as ether. The neutral compound is then separated from the aqueous portion, dried, and treated with the requisite acid or base to give the desired salt.

Also included within the scope of the invention are solvates of the invention. The formation of the solvate will vary depending on the compound and solvent used. In general, solvates are formed by dissolving the compound in the appropriate solvent and isolating the solvate by cooling or using an antisolvent. The solvate is typically dried or azeotroped under ambient conditions.

Prodrugs of compounds of Formula I or III may be conventional esters with available hydroxyl (or thiol) or carboxyl groups. For example, when one of $R^1$–$R^3$ or $R^5$–$R^6$ is OH in a compound of Formula I or III, it may be acylated using an activated acid in the presense of a base and, optionally, in inert solvent (e.g. an acid chloride in pyridine). Also, when $R^1$ is $CO_2R^{16}$ in a compound of Formula I, wherein $R^{16}$ is H, an ester may be formed by activation of the hydroxyl group of the acid and treatment with the appropriate alcohol in the presence of a base in an inert solvent. Some common esters which have been utilized as prodrugs are phenyl esters, aliphatic ($C_1$–$C_{24}$) esters, acyloxymethyl esters, carbamates and amino acid esters. Prodrugs of compounds of Formulae I and III may also be formed by functional derivatization of substituents containing an acidic NH group, for example, compounds of Formula I or III where, $R^{10}$ is $C(O)NHR^{13}$, $SO_2NHR^{13}$ and $C(S)NHR^{13}$ or compounds of Formula I, where $R^1$ is $C(O)NR^{14}R^{15}$, $SO_2NR^{14}R^{15}$, $NHC(NR^{18})R^{17}$ or $C(NR^{19})NR^{20}R^{21}$ and one of the groups attached to a nitrogen is H. Some common prodrugs for amides, imides and other NH-acidic compounds are N-Mannich bases, N-hydroxymethyl derivatives, N-acyloxyalkyl derivatives, and N-acyl derivatives.

In accordance with another of its aspects, the compounds of the present invention can be prepared by processes analogous to those established in the art. For example, compounds of Formulae I and III, wherein $R^4$ is $C_{1-4}$alkyl, may be prepared from another compound of Formula I or III, wherein $R^4$ is H, by alkylation of the indole nitrogen using standard conditions. Such conditions may involve treating the NH compound with a strong base such as sodium hydride or sodium hexamethyldisilazide at low temperatures, for example –78–0° C., and in an inert solvent such as tetrahydrofuran, followed by the addition of a reagent of the formula $R^4$—Y, wherein $R^4$ is $C_{1-4}$alkyl and Y is a suitable leaving group such as halo (for example bromo).

Compounds of Formula Ia and Ia', wherein $R^1$–$R^3$ and n are as defined in Formula I, $R^4$ is H, Z is C and - - - - - represents a double bond, may be prepared, as shown in Scheme 1, by condensing a compound of Formula A, wherein $R^1$ is as defined in Formula I, with a reagent of Formula B, wherein $R^2$, $R^3$ and n are as defined in Formula I, either in acidic or basic conditions in a suitable solvent, to provide compounds of Formula Ia and Ia', wherein $R^1$–$R^3$ and n are as defined in Formula I, $R^4$ is H, Z is C and - - - - - represents a double bond. Suitable basic conditions include organic amines such as pyrrolidine or triethylamine in solvents such as methanol, ethanol and the like. Preferred basic conditions are pyrrolidine in ethanol at a refluxing temperature. Suitable acidic conditions include, for example, trifluoroacetic acid in acetic acid at a temperature in the range of 90–120° C., preferably at around 110° C. When the reaction of compound A with compound B is carried out in basic conditions, typically the regioisomer corresponding to Ia is the sole product formed. Under acidic conditions, both regioisomeric alkenes, Ia and Ia', may be isolated, the ratio of which will vary depending on reaction conditions and the identity and position of $R^2$. The Compounds of Formula Ia and Ia', wherein $R^1$–$R^3$ and n are as defined in Formula I, $R^4$ is H, Z is C and - - - - - represents a double bond, may be reduced using standard hydrogenation conditions, ionic hydrogenation conditions or using metal hydride reducing reagents to provide compounds of Formula Ib, wherein $R^1$–$R^3$ and n are as defined in Formula I, $R^4$ is H, Z is C and - - - - - represents a single bond as shown in Scheme 1. Preferred is reduction by hydrogenation, using a suitable catalyst such as palladium or platinum on carbon in methanol or ethanol at room temperature, or reduction by ionic hydrogenation using a mixture if a trialkylsilane, preferably triethylsilane, and an acid such as trifluoracetic acid, in a nonpolar solvent such as dichloromethane at room temperature.

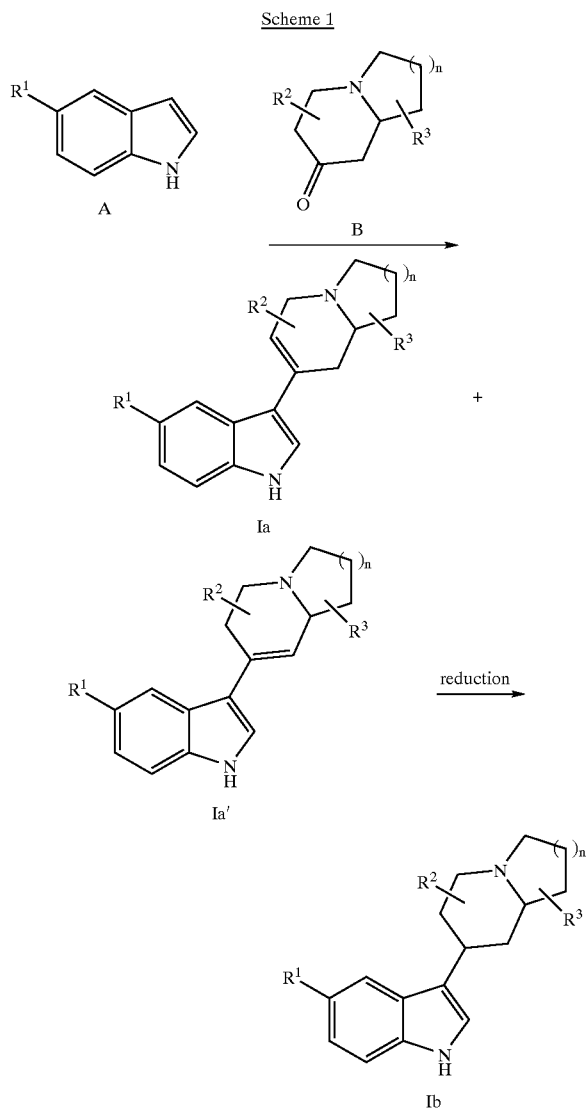

Scheme 1

Compounds of Formula Ic, wherein $R^1$–$R^3$ and n are as defined in Formula I, $R^4$ is H, Z is N and - - - - - is a single bond, may be prepared as shown in Scheme 2. A compound of Formula C or a compound of Formula D, wherein $R^1$ is as defined in Formula I, and PG is a suitable protecting group such as acetate or tosyl, may be reacted with a bicyclic piperazine of Formula E, wherein $R^2$, $R^3$ and n are as defined in Formula I, in the presence of a catalytic amount of an acid, such as p-toluenesulfonic acid or camphorsulfonic acid, in an inert solvent such as toluene or benzene, at temperatures in the range of 25–120° C., preferably at refluxing temperatures. Removal of the protecting group under standard conditions, for example, an alkali base such as sodium hydroxide in a polar solvent such as methanol at temperatures in the range of 20–100° C., suitably 50–80° C., for removal of an acetate group, provides compounds of Formula Ic, wherein $R^1$–$R^3$ and n are as defined in Formula I, $R^4$ is H, Z is N and - - - - - is a single bond.

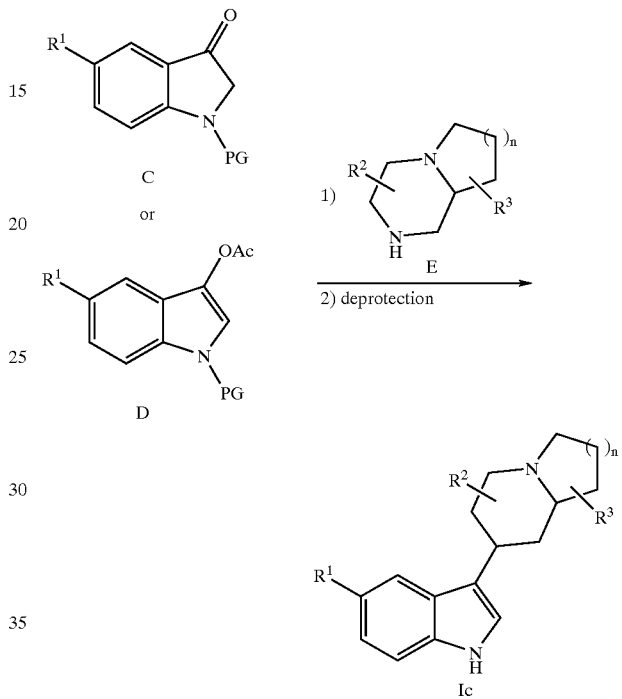

Scheme 2

Compounds of Formula A, wherein $R^1$ is as defined in Formula I, are either commercially available or can be prepared using standard procedures. For example, compounds of Formula A may be prepared using the well known Fischer indolization method (see March, *J, Advanced Organic Chemistry*, John Wiley & Sons, 1985, p. 1032–1033, and references found therein) or using the procedure shown in Scheme 3. 4-Substituted anilines of Formula F, wherein $R^1$ is as defined in Formula I, can be treated with reagents of Formula G, in the presence of a base such as sodium bicarbonate or potassium carbonate in an alcoholic solvent at temperatures in the range of 60–100° C., to provide intermediates of Formula H. Preferred conditions are sodium bicarbonate in ethanol at around 80° C. Intermediates of Formula H can be cyclized in the presence of reagents of Formula J, wherein R is, for example, methyl or trifluoromethyl (which is preferred) at temperatures in the range of 60–100° C., to provide indoles of Formula K. The preferred conditions are trifluoroacetic anhydride and trifluoroacetic acid at refluxing temperatures. Finally, compounds of Formula K can be treated under standard deprotection conditions, for example alkali hydroxides in an alcoholic solvent, to provide indoles of Formula A, wherein $R^1$ is as defined in Formula I. Preferred conditions for this reaction are potassium hydroxide in ethanol at room temperature. The reagents of Formula F and G, are either commercially available or can be prepared using processes analogous to those established in the art.

Scheme 3

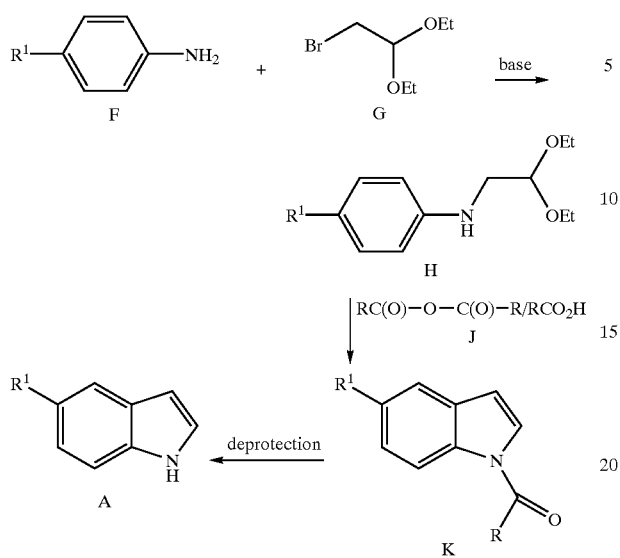

Compounds of Formula A, wherein $R^1$ is specifically a group of Formula II, can be prepared, as shown below in Scheme 4. An indole reagent of Formula L, wherein Y is a suitable leaving group such as halo, (preferably bromo or iodo), and PG is a suitable protecting group, such a trialkylsilyl, arylsulfonyl or alkylsulfonyl group, preferably t-butyldimethylsilyl, can be treated with strong base, such as an alkyllithium, preferably t-butyllithium, followed by the addition of a ketone of Formula M, wherein X and $R^5$ are as defined in Formula I, to provide compounds of Formula N, wherein $R^5$, X and PG are as defined above. This reaction is performed in inert solvents, such as ether or tetrahydrofuran, at temperatures ranging from –100 to 0° C. Preferred conditions are tetrahydrofuran at –78° C. It should be noted that if two equivalents of a strong base (for example, potassium hydride followed by t-butyllithium) are used in this reaction, it may not be necessary to protect the indole nitrogen. Removal of the protecting group on the indole nitrogen may be performed using standard procedures. For example, when PG is a trialkylsilyl group such as t-butyldimethylsilyl, compounds of Formula N are suitably deprotected using tetrabutylammonium fluoride in THF at room temperature, to provide compounds of Formula A(i), wherein X and $R^5$ are as defined in Formula I. Compounds of Formula A(i) may be dehydrated under standard conditions, for example, formation of the mesylate and elimination under basic conditions or in the presence of an acid such as trifluoroacetic acid in an inert solvent such as tetrahydrofuran, to provide compounds of Formula A(ii), wherein X and $R^5$ are as defined in Formula I, as shown in Scheme 4. It should be noted that when $R^5$ is other than H, a mixture of regioisomeric alkenes may be obtained. Compounds of Formula A (ii) may be reduced using standard hydrogenation conditions or using metal hydride reducing reagents to provide compounds of Formula A(iii), wherein X and $R^5$ are as defined in Formula I, as shown in Scheme 4. Preferred is reduction by hydrogenation, using a suitable catalyst such as palladium or platinum on carbon in methanol or ethanol at room temperature.

Scheme 4

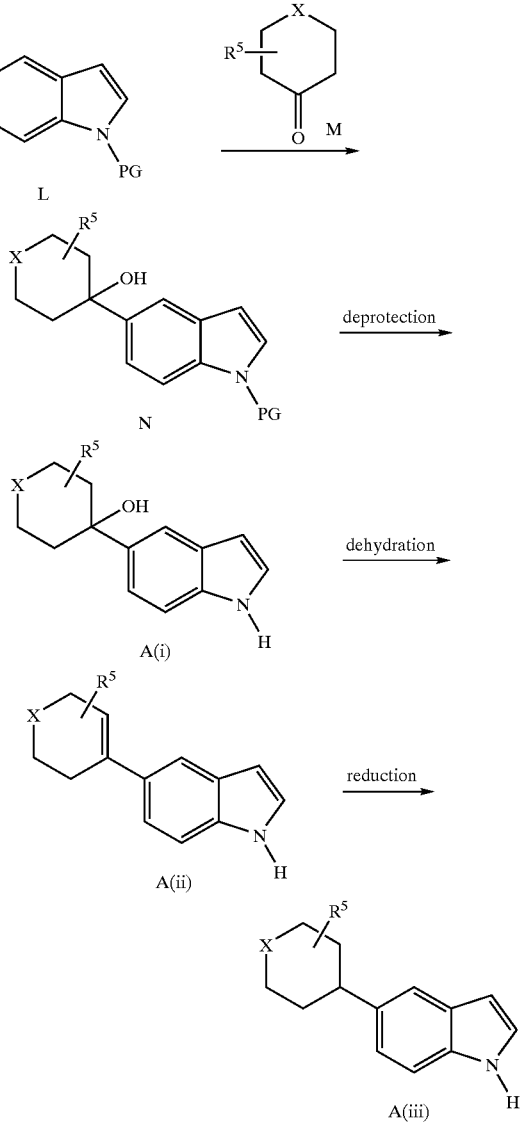

An alternate route to the preparation of compounds of Formula A(ii) is shown in Scheme 5. An indole of Formula L, wherein Y is a suitable leaving group such as halo or triflate (preferably bromo) and PG is an appropriate protecting group, such as acetate, may be coupled with with a vinyl trialkylstannane of, for example, Formula P or Q, wherein $R^5$ and X are as defined in Formula I, under standard metal catalyzed-cross coupling condition. It will be appreciated that other metal coupling groups could be used in place of the vinyl stannane, for example, a vinyl boronic acid, chloro zinc and the like. Suitable coupling conditions include refluxing the indole and cyclic metal reagent in an inert solvent, such as dimethylformamide, toluene or tetrahydrofuran, in the presence of a palladium catalyst such as tetrakis(triphenylphosphine) palladium (0). Removal of the protecting group using standard conditions, for example sodium hydroxide in methanol to remove an acetate group, provides compounds of Formula A(ii) (as possible regioisomeric alkenes), wherein $R^5$ and X are as defined in Formula I. This metal-catalyzed cross-coupling procedure could also be applied to the preparation of compounds of Formula A where $R^1$ is vinyl or optionally substituted phenyl, thienyl or furanyl by replacing the reagent of Formula P or Q above with the appropriate metal-containing reagent. It should also be noted that certain $R^1$ groups may be converted to other $R^1$ groups using standard procedures, for example alkylation, acylation, oxidation and reduction.

Scheme 5

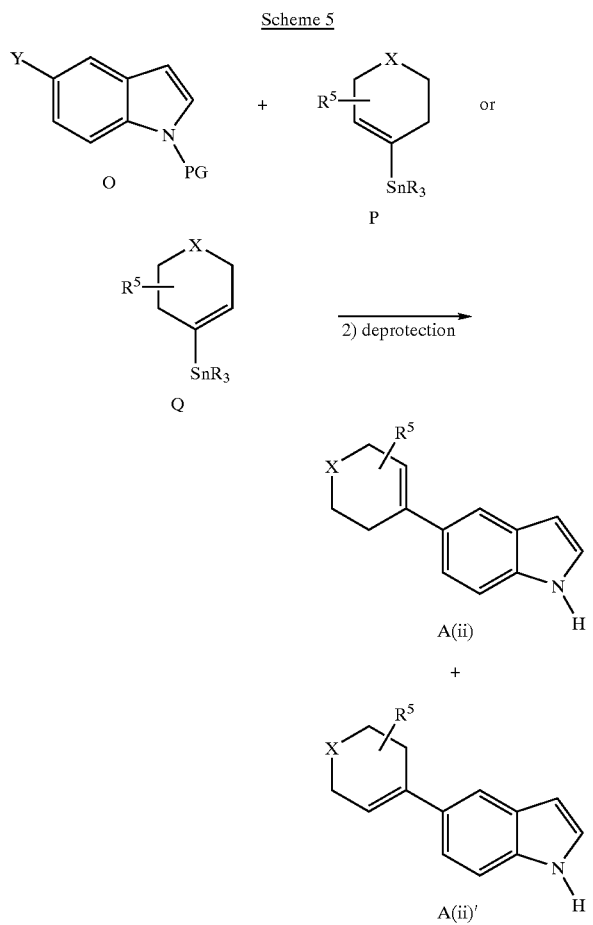

The bicyclic piperidinones B and piperizines E, wherein $R^2$, $R^3$ and n are as defined in Formula I, are either commercially available or can be prepared using procedures known in the art. For example, bicyclic piperidinones of Formula B may be prepared according to procedures described in King, F. D., J. Chem. Soc. Perkin Trans. I, 1986:447–453 and bicyclic piperazines of Formula E may be prepared according to procedures described in Power, P. et al., U.S. Pat. No. 5,576,314; Saleh, M. A. et al. J. Org. Chem. 58, 1993:690–695; Urban, F. J. Heterocyclic Chem. 32, 1995:857–861; Bright, G. et al. WO 90/08148; de Costa, B. R. et al. J. Med. Chem. 36, 1993:2311–2320; and Botre, C. et al. J. Med. Chem. 29, 1986:1814–1820. The cyclic stannanes P and Q may be prepared from the corresponding keto compound M using standard chemistries, for example, by reacting the ketone with a base, such as lithium diisopropylamide or triethylamine, and a suitable triflating agent, such as N-phenyltriflimide or triflic anhydride, and converting the resulting triflate to a compound of Formula P or Q by treatment with, for example, a palladium catalyst and a bis(trialkyltin). Alternatively, cyclic stannanes P and Q may be prepared by forming the tosylhydrazone of the corresponding keto compound M and, using standard Shapiro conditions, trapping the vinyl anion with a suitable reagent like tributyltin chloride.

Compounds of Formula L may be prepared from compounds of Formula O using standard protecting group methodologies. For example, the t-butyldimethylsilyl protecting group may be attached to the indole nitrogen by treating a compound of Formula O, wherein Y is as defined above, with a strong base, such as sodium hexamethyldisilazide, in an inert solvent, such as tetrahydrofuran, at a temperature in the range of −40 to 30° C., suitably 25° C., followed by the addition of t-butyldimethylsilyl chloride at a reduced temperature, suitably 0° C. Compounds of Formulae C and D are known or may be prepared using standard chemistries.

It should be noted that one skilled in the art would realize that the sequence of reactions described above for the preparation of compounds of Formulae I and III can be varied. For example, the group at the indole 3-position may be incorporated into the molecule before the addition of the group at the indole 5-position.

In some cases, the chemistries outlined above may have to be modified, for instance by use of protecting groups, to prevent side reactions due to reactive groups, such as reactive groups attached as substituents. This may be achieved be means of conventional protecting groups, as described in *Protective Groups in Organic Chemistry*, ed. McOmie, J. F. W. Plenum Press, 1973; and Greene, T. W. & Wuts, P. G. M., *Protective Groups in Organic Synthesis*, John Wiley & Sons, 1991.

In another embodiment of the invention, the present compounds can be used to distinguish 5-$HT_{1D}$ receptors from other receptor subtypes, for example glutamate or opioid receptors, within a population of receptors, and in particular to distinguish between the 5-$HT_{1D}$ and other 5-HT receptor subtypes. The latter can be achieved by incubating preparations of the 5-$HT_{1D}$ receptor and one of the other 5-HT receptor subtypes (for example 5-$HT_{1B}$) with a 5-$HT_{1D}$-selective compound of the invention and then incubating the resulting preparation with a radiolabeled serotonin receptor ligand, for example [$^3$H]-serotonin. The 5-$HT_{1D}$ receptors are then distinguished by determining the difference in membrane-bound activity, with the 5-$HT_{1D}$ receptor exhibiting lesser radioactivity, i.e., lesser [$^3$H]-serotonin binding, than the other 5-HT receptor subtype.

In an aspect of the invention, the compound is provided in labeled form, such as radiolabeled form, e.g. labeled by incorporation within its structure $^3$H or $^{14}$C or by conjugation to $^{125}$I. In another aspect of the invention, the compounds in labeled form can be used as competitive ligands to identify 5-$HT_{1D}$ receptor ligands by techniques common in the art. This can be achieved by incubating the receptor or tissue in the presence of a ligand candidate and then incubating the resulting preparation with an equimolar amount of radiolabeled compound of the invention such as [$^3$H]-5-isopropyl-3-[(8a-R,S)-1,2,3,5,8,8a-hexahydro-7-indolizinyl]-1H-indole. 5-$HT_{1D}$ receptor ligands are thus revealed as those that are not significantly displaced by the radiolabeled compound of the present invention. Alternatively, 5-$HT_{1D}$ receptor ligand candidates may be identified by first incubating a radiolabeled form of a compound of the invention then incubating the resulting preparation in the presence of the candidate ligand. A more potent 5-$HT_{1D}$ receptor ligand will, at equimolar concentration, displace the radiolabeled compound of the invention.

A radiolabelled compound of Formula I or III may be prepared using standard methods known in the art. For example, tritium may be incorporated into a compound of Formula I or III using standard techniques, for example by hydrogenation of a suitable precursor to a compound of Formula I using tritium gas and a catalyst. Alternatively, a compound of Formula III wherein $R^1$ is radioactive iodo may be prepared from the corresponding tialkyltin (suitably timethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis (triphenylphosphine) palladium (0) in an inert solvent, such as dioxane, and at elevated temperatures, suitably 50–100° C.

The present compounds are useful as pharmaceuticals for the treatment of various conditions in which the use of a 5-HT$_{1D}$ ligand is indicated, such as for the treatment of migraine, cluster headache and portal tension, a condition characterized by increased portal vein blood flow and typically associated with cirrhosis of the liver.

For use in medicine, the compounds of the present invention can be administered in a standard pharmaceutical composition. The present invention therefore provides, in a further aspect, pharmaceutical compositions comprising a pharmaceutically acceptable carrier and at least one compound of Formula I, or a pharmaceutically acceptable salt, solvate or hydrate thereof, in an amount effective to stimulate the 5-HT$_{1D}$ receptor.

The compounds of the present invention may be administered by any convenient route, for example by oral, parenteral, buccal, sublingual, nasal, rectal or transdermal administration and the pharmaceutical compositions will be formulated accordingly.

Compounds of Formula I and their stereoisomers, solvates, hydrates or pharmaceutically acceptable salts for oral administration can be formulated as liquids, for example syrups, suspensions, solutions or emulsions, or as solid forms such as tablets, capsules and lozenges, or they may be presented as a dry product for constitution with water or other suitable vehicle before use. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent (e.g. sorbitol syrup, methyl cellulose or hydrogenated edible fats), preservative (e.g. methyl or propyl p-hydroxybenzoates or sorbic acid), flavouring or colouring agent. A composition in the form of a tablet can be prepared using any, suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

The compounds of the invention may be formulated for parenteral administration by injection, including using conventional catheterisation techniques or infusion. Formulations for injection may be presented in unit dosage form, e.g. in ampoules or in multi-dose containers, with an added preservative. Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil, and may contain formulatory agents such as suspending, stabilizing and/or dispersing agents. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer. Capsules and cartridges of e.g. gelatin for use in an inhaler or atomizing device may be formulated containing a powder mix of a compound of the invention and a suitable powder base such as lactose or starch.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of for example suppositories or retention enemas, containing a conventional suppository base such as cocoa butter or other glycerides.

A proposed dose of the compounds of the invention for oral, buccal, sublingual or rectal administration to human (about 70 kg body weight) for the treatment of migraine is 0.1 mg to 500 mg, for example 0.5 mg to 100 mg, preferably. 1 mg to 50 mg, of active ingredient per dose which could be administered up to 8 times per day, more usually 1 to 4 times per day. It will be appreciated that it may be necessary to make routine changes to the dosage depending on the age and weight of the patent as well as the severity of the condition to be treated. It should be understood that unless otherwise indicated, the dosages are referred to in terms of the weight of the compound of Formula I calculated as the free base.

The overall daily dosage administered by injection may be in the range of 0.01 mg to 100 mg, preferably between 0.1 mg and 50 mg, e.g., between 1 mg and 25 mg, of a compound of Formula I or a pharmaceutically acceptable salt, solvate or hydrate thereof calculated as the free base, the compound being administered 1 to 4 doses per day.

Aerosol formulations are preferably arranged so that each metered dose or "puff" delivered from a pressurized aerosol contains 0.1 to 10 mg of a compound of the invention, and each dose administered via capsules and cartridges in an inhaler contains 0.1 to 50 mg of a compound of the invention. Administration may be several times daily, for example 2 to 8 times, giving for example 1,2 or 3 doses each time. The overall daily dose by inhalation will be similar to that for oral administration.

The compounds of the invention may, if desired, be administered in combination with one or more other therapeutic agents, such as analgesics, anti-inflammatory agents and anti-nauseants.

EXPERIMENTAL EXAMPLES

Example 1(a)

1-(1H-Indol-5-yl)-N-methyl-4-azacyclohexanol

To a solution of 5-bromo-1H-indole (5.0 g, 25.5 mmol) in THF at −10° C. under argon, was added a solution of potassium hydride (1.13 g, 28.1 mmol) in THF (7 mL). The reaction mixture was then cooled to −78° C., and t-butyllithium (52.5 mL of a 1.7 M solution in pentane, 89.3 mmol) was added slowly, via syringe. The mixture was stirred for 15 minutes, and 1-methyl-4-piperidone (6.75 mL, 54.8 mmol) was quickly added. After the mixture was stirred at −78 ° C. for one hour, the solution was warmed to −20° C. and poured into a mixture of a buffer solution (20 mL, pH 7.0) and ethyl acetate (30 mL). The organic layer was washed with brine (30 mL) and dried ($Na_2SO_4$). The product was purified by column chromatography over silica gel using 5% 2M ammonia in methanol in dichloromethane as the eluent to provide the title compound (1.95 g, 35%).

In a like manner, the following additional compound was prepared:
(b) 1-(1H-Indol-5-yl)cyclohexanol (1.95g 35%): from 5-bromo-1H-indole (5 g, 25.5 mmol) with KH (1.127 g, 28.1 mmol) in THF at −10° C., then treated with 1.7 M t-BuLi in pentane (37.5 mL, 63.8 mmol) and cyclohexanone (5.68 mL, 54.8 mmol) at −78° C.

Example 2

1H-Indol-5-yl-phenylmethanone

5-Bromoindole(1.0 g, 5.10 mmol) was dissolved in THF (10 mL) and the resulting solution was cooled to −78° C. t-Butyl lithium (1.7 M in pentane, 10.5 mL, 17.9 mmol) was added dropwise and the solution stirred for 30 minutes before being added to a solution of benzoyl chloride (0.86 g, 6.12 mmol) in THF (10 mL) at −78° C. via cannula. The reaction mixture was allowed to warm to room temperature and was stirred overnight and was then quenched with saturated ammonium chloride and diluted with ethyl acetate. The organic phase was washed with water and brine, dried ($Na_2SO_4$), filtered and concentrated. Silica gel chromatography using 20% hexane in ethyl acetate as the eluent provided the title compound as a beige solid (0.40 g, 35%).

Example 3(a)

5-Fluoro-3-[(8a-R,S)-1,2,3,5,8,8a-hexahydro-7-indolizinyl]-1H-indole

5-Fluoro-1H-indole (1.0 g, 7.4 mmoles), (8a-R,S)-octahydroindblizin-7-one (King, F. D., J. Chem. Soc. Perkin Trans. 1, 1986:447–453, 1.03 g, 7.4 mmoles) and pyrrolidine (6.6 mL, 74 mmoles) were mixed in ethanol (10 mL) and refluxed for 72 hours. The resulting solid was collected by filtration, washed with methanol and dried to provide the title compound (1.48 g, 78%). HRMS-FAB $MH^+$ for $C_{16}H_{17}FN_2$: calc'd 257.14542, found 257.14373.

In a like manner, the following additional compounds were prepared:
(b) 5-Methoxy-3-[(8a-R,S)-1,2,3,5,8,8a-hexahydro-7-indolizinyl]-1H-indole: from 5-methoxy-1H-indole, 63%. HRMS-FAB $MH^+$ for $C_{17}H_{20}N_2O$: calc'd 269.16539, found 269.16418.
(c) 5-Methyl-3-[(8a-R,S)-1,2,3,5,8,8a-hexahydro-7-indolizinyl]-1H-indole: from 5-methyl-1H-indole, 21%. HRMS-FAB $MH^+$ for $C_{17}H_{20}N_2$: calc'd 253.17047, found 253.16924.
(d) 5-Isopropyl-3-[(8a-R,S)-1,2,3,5,8,8a-hexahydro-7-indolizinyl]-1H-indole: from 5-isopropyl-1H-indole, 37%.
(e) 5-Bromo-3-[(8a-R,S)-1,2,3,5,8,8a-hexahydro-7-indolizinyl]-1H-indole: from 5-bromo-1H-indole, 73%.
(f) 5-Cyclohexyloxy-3-[(8a-R,S)-1,2,3,5,8,8a-hexahydro-7-indolizinyl]-1H-indole: from 5-cyclohexyloxy-1H-indole, 37%.
(g) 5-(2-Thienyl)-3-[(8a-R,S)-1,2,3,5,8,8a-hexahydro-7-indolizinyl]-1H-indole: from 5-(2-thienyl)-1H-indole, 56%.
(h) 1-{[3-(8a-R,S)-1,2,3,5,8,8a-Hexahydro-7-indolizinyl]-1H-indol-5-yl}cyclohexanol: from 1-(1H-indol-5-yl)cyclohexanol (Example 1b), 64%.
(i) 1-{[3-(8a-R,S)-1,2,3,5,8,8a-Hexahydro-7-indolizinyl]-1H-indol-5-yl}-N-methyl4-azacyclohexanol: from 1-(1H-indol-5-yl)-N-methyl-4-azacyclohexanol (Example 1a), 54%.
(j) {3-[(8a-R,S)-1,2,3,5,8,8a-Hexahydro-7-indolizinyl]-1H-indol-5-yl}phenylmethanone: from 1H-indol-5-yl-phenylmethanone (Example 2), 37%.

Example 4

5-Bromo-1-(t-butyldimethylsilyl)-3-[(8a-R,S)-1,2,3,5,8,8a-hexahydro-7-indolizinyl]indole To a solution of 5-bromo-3-[(8a-R,S)-1,2,3,5,8,8a-hexahydro-7-indolizinyl]-1H-indole (Example 3e, 0.5 g, 1.58 mmol) in THF (10 mL) under argon, was added sodium hexamethyldisilazide (3.15 mL, 3.15 mmol) and the resulting solution was stirred at room temperature for 20 min. The reaction mixture was cooled to 0° C. and to this was added a solution of t-butyldimethylsilyl chloride (0.474 g, 3.15 mmol) in THF (4 mL) and the resulting mixture was warmed to room temperature and stirred for 1 hour. The solvent was removed in vacuo and the resulting product was diluted with water (10 mL) and extracted with ethyl acetate (2×10 mL). The ethyl acetate extract was washed with brine (10 mL), dried ($Na_2SO_4$), filtered and the filtrate was evaporated to dryness. The crude residue was subjected to flash silica gel chromatography to afford the title compound quantitatively.

Example 5

1-{[3-(8a-R,S)-1,2,3,5,8,8a-Hexahydro-7-indolizinyl]-1-(t-butyldimethylsilyl)indol-5-yl}tetrahydro-2H-thiopyran-4-ol In a 25 mL flame dried, round bottom flask equipped with a stir bar under argon was added 5-bromo-1-(t-butyldimethylsilyl)-3-[(8a-R,S)-1,2,3,5,8,8a-hexahydro-7-indolizinyl]indole (Example 4, 350 mg, 0.81 mmol) and THF (8 mL). The mixture was cooled to −78° C. and t-butyllithium (1.7 M in hexane, 1.19 mL, 2.03 mmol) was added dropwise. The resulting mixture was stirred at −78° C. for 50 min., followed by the addition of a solution of tetrahydrothiopyran-4-one (236 mg, 2.03 mmol) in THF (4 mL). The resulting mixture was warmed up to −5° C. and stirred for a further 1 hour. The reaction mixture was then poured into a pH 7 buffer (5 mL) at 0° C., extracted into ethyl acetate (2×10 mL) and the combined organic phases were washed successively with water (10 mL) and brine (10 mL). The organic layer was dried ($Na_2SO_4$), filtered and the filtrate was evaporated to dryness in vacuo. The crude residue was subjected to flash silica gel chromatography to afford the title compound (229 mg, 60%).

Example 6

5-Isopropyl-3-[(8a,R,S)-6-methyl-1,2,3,5,8,8a-hexahydro-7-indolizinyl]-1H-indole To a solution of (8-R,S)(8a-R,S)-8-methylhexahydroindolizin-7(1H)-one (0.50 g, 3.26 mmol)

in a mixture of trifluoroacetic acid (1 mL) and acetic acid (0.75 mL) kept at 110° C., was added, dropwise, a solution of 5-isopropylindole (0.15 g, 0.942 mmol) in acetic acid (0.75 mL). The mixture was then stirred at 110° C. for 0.5 hour, poured into water (5 mL) and the pH of the solution was adjusted until it was basic using a 1M potassium hydroxide solution. The product was extracted into dichloromethane (2×10 mL), dried ($Na_2SO_4$), and the solvent removed in vacuo to provide the title compound as a green yellow solid (0.103 g, 37%).

Example 7

4-{[3-(8a-R,S)-1,2,3,5,8,8a-Hexahydro-7-indolizinyl]-1H-indol-5-yl}tetrahydro-2H-pyran-4-ol To a solution of 5-bromo-3-[(8a-R,S)-1,2,3,5,8,8a-hexahydro-7-indolizinyl]-1H-indole (Example 3e, 500 mg, 1.58 mmol) in THF at −10° C. under argon, was added a solution of potassium hydride (70 mg, 1.74 mmol) in THF (7 mL). The reaction mixture was then cooled to −78° C., and t-butyllithium (2.32 mL of a 1.7 M solution in pentane, 3.93 mmol) was slowly introduced via syringe. The mixture was stirred for 15 minutes, and tetrahydropyran-4-one (474 mg, mmole) was quickly added. After the mixture was stirred at −78 ° C. for one hour, the solution was warmed to −20° C. and poured into a mixture of a buffer solution (20 mL, pH 7.0) and ethyl acetate (30 mL). The organic layer was washed with brine (30 mL) and dried ($Na_2SO_4$). The product was purified by column chromatography over silica gel using 5% 2M ammonia in methanol in dichloromethane as the eluent. The title compound was isolated as a white powder (82.3 mg, 15%).

Example 8(a)

5-(5,6-Dihydro-2H-pyran-4-yl)-3-[(8a-R,S)-1,2,3,5,8,8a-hexahydro-7-indolizinyl]-1H-indole and 8(b): 5-(5,6-Dihydro-2H-pyran-4-yl)-3-[(8a-R,S)-1,2,3,5,6,8a-hexahydro-7-indolizinyl]-1H-indole 4-{[3-(8a-R,S)-1,2,3,5,8,8a-Hexahydro-7-indolizinyl]-1H-indol-5-yl}tetrahydro-2H-pyran-4-ol (Example 7, 76 mg, 0.225 mmol) was added to a solution of THF (2.3 mL) and TFA (0.46 mL). The reaction mixture was stirred at 70° C. for 2 hours, then the solvents were removed in vacuo and the product purified using silica gel chromatography with 2% 2M ammonia/methanol in dichloromethane as the eluent. Two products were isolated: 5-(5,6-dihydro-2H-pyran-4-yl)-3-[(8a-R,S)-1,2,3,5,8,8a-hexahydro-7-indolizinyl]-1H-indole (43.2 mg, 60.8%) and 5-(5,6-dihydro-2H-pyran-4-yl)-3-[(8a-R,S)-1,2,3,5,6,8a-hexahydro-7-indolizinyl]-1H-indole (23.8 mg, 33.5%).

In a like manner, the following additional compounds were prepared:

(c) 5-(Cyclohexen-1-yl)-3-[(8a-R,S)-1,2,3,5,8,8a-hexahydro-7-indolizinyl]-1H-indole (78 mg, 35%) and (d): 5-(Cyclohexen-1-yl)-3-[(8a-R,S)-1,2,3,5,6,8a-hexahydro-7-indolizinyl]-1H-indole (73.5 mg, 33%): from 1-{[3-(8a-R,S)-1,2,3,5,8,8a-hexahydro-7-indolizinyl]-1H-indol-5-yl}cyclohexanol (Example 3h, 224.3 mg, 0.67 mmol) and TFA (1.34 mL) in THF (6.7 mL) at 70° C., overnight.

(e) 5-(5,6-Dihydro-2H-thiopyran-4-yl)-3-[(8a-R,S)-1,2,3,5,8,8a-hexahydro-7-indolizinyl]-1H-indole (12.7 mg, 27%) and (f) 5-(5,6-Dihydro-2H-thiopyran-4-yl)-3-[(8a-R,S)-1,2,3,5,6,8a-hexahydro-7-indolizinyl]-1H-indole (15.1 mg, 32%): from 1-{[3-(8a-R,S)-1,2,3,5,8,8a-hexahydro-7-indolizinyl]-1-(t-butyldimethylsilyl)indol-5-yl}tetrahydro-2H-thiopyran-4-ol (Example 5, 66.2 mg, 0.14 mmol) and TFA (0.6 mL) in THF (2 mL) at 70° C., overnight.

Example 9(a)

5-Fluoro-3-[(7R or 7S)(8a-R,S)-octahydro-7-indolizinyl]-1H-indole, Isomer I and 9(b) 5-Fluoro-3-[(7R or 7S)(8a-R,S)-octahydro-7-indolizinyl]-1H-indole, Isomer II 5-Fluoro-3-[(8a-R,S)-1,2,3,5,8,8a-hexahydro-7-indolizinyl]-1H-indole (Example 3a, 500 mg, 1.95 mmol) and 10% Pd/C (250 mg) in ethanol (5 mL) were reacted under an atmosphere of $H_2$ at room temperature overnight. The resulting solution was filtered, evaporated and the product purified by silica gel chromatography using 2% 2M ammonia/methanol in dichloromethane as the eluent to provide two, separable diastereoisomers: 5-fluoro-3-[(7R or 7S, 8-R,S)-octahydro-7-indolizinyl]-1H-indole, Isomer I (300 mg, 59%) and 5-fluoro-3-[(7R or 7S, 8-R,S)-octahydro-7-indolizinyl]-1H-indole, Isomer II (88 mg, 17%). HRMS-FAB $MH^+$ for $C_{16}H_{19}N_2F$: calc'd 259.16105, found 259.16323 (isomer I) and 259.16104 (isomer II).

In a like manner the following additional compounds were prepared:

(c) 5-Isopropyl-3-[(7R or 7S)(8a-R,S)-octahydro-7-indolizinyl]-1H-indole, Isomer I (53.2 mg, 44.1%) and (d) 5-Isopropyl-3-[(7R or 7S)(8a-R,S)-octahydro-7-indolizinyl]-1H-indole, Isomer II (7.8 mg, 6.4%): from 5-isopropyl-3-[(8a-R,S)-1,2,3,5,8,8a-hexahydro-7-indolizinyl]-1H-indole (Example 3d, 120 mg, 0.43 mmol) and 10% Pd/C (240 mg) in ethanol (2 mL) under $H_2$ at RT.

(e) 5-Methoxy-[(7R or 7S)(8a-R,S)-octahydro-7-indolizinyl]-1H-indole, Isomer I (152.7 mg, 58.7%) and (f) 5-Methoxy-3-[(7R or 7S)(8a-R,S)-octahydro-7-indolizinyl]-1H-indole, Isomer II (47.1 mg, 18.1%): from 5-methoxy-3-[(8a-R,S)-1,2,3,5,8,8a-hexahydro-7-indolizinyl]-1H-indole (Example 3b, 258.2 mg, 0.962 mmol) and 10% Pd/C (200 mg) in ethanol (3 mL) under $H_2$ at RT.

(g) 5-(Tetrahydropyran-4-yl)-[(7-R,S)(8a-R,S)-octahydro-7-indolizinyl]-1H-indole, (8.0 mg, 24.7%): from a mixture of 5-(5,6-dihydro-2H-pyran-4-yl)-3-[(8a-R,S)-1,2,3,5,8,8a-hexahydro-7-indolizinyl]-1H-indole (Example 8a) and 5-(5,6-dihydro-2H-pyran-4-yl)-3-[(8a-R,S)-1,2,3,5,6,8a-hexahydro-7-indolizinyl]-1H-indole (Example 8b) (32 mg, 0.1 mmol) and 10% Pd/C (60 mg) in ethanol (2 mL) under $H_2$ at RT.

(h) {3-[(7R or 7S)(8a-R,S)-Octahydro-7-indolizinyl]1H-indol-5-yl}phenylmethanone, Isomer I (24.0 mg, 48%) and (i) {3-[(7R or 7S)(8a-R,S)-Octahydro-7-indolizinyl]1H-indol-5-yl}phenylmethanone, Isomer II (6.5 mg, 13%): from {3-[(8a-R,S)-1,2,3,5,8,8a-hexahydro-7-indolizinyl]-1H-indol-5-yl}phenylmethanone (Example 3j, 49.2 mg, 0.144 mmol) and 10% of Pd/C (50.7 mg) in ethanol (2 mL) under $H_2$ at RT.

Example 10

5-Bromo-3-[(7-R,S)(8a-R,S)-octahydro-7-indolizinyl]-1H-indole

5-Bromo-3-[(8a-R,S)-1,2,3,5,8,8a-hexahydro-7-indolizinyl]-1H-indole (Example 3e, 0.573 g, 1.8 mmol) was mixed with triethylsilane(2.1 g, 18 mmol) in dichloromethane under argon. Trifluoroacetic acid (6.16 g 54 mmol) was then added to the reaction mixture dropwise, and the resulting solution was stirred for 20 minutes at room temperature. The product was purified by column chromatography using 4~5% 2M ammonia/methanol in dichloromethane as the eluent to provide the title compound (0.40 g, 69.%).

Example 11

1-Acetyl-5-bromo-3-[(7-R,S)(8a-R,S)-octahydro-7-indolizinyl]indole

To a solution of 5-bromo-3-[(7-R,S)(8a-R,S)-octahydro-7-indolizinyl]-1H-indole (Example 10, 365 mg, 1.14 mmol) in THF (5 mL) cooled to 0° C. under argon, was added sodium bis(trimethylsilyl)amide (1M solution in THF, 3.1 mL, 3.1 mmol) and the resulting solution was stirred for 5 minutes. Acetyl chloride (0.18 g, 2.25 mmol) was then added and the solution stirred for 2 hours. Silica gel (2 g) and 2 drops of water were then added to quench the reaction and the resulting slurry was applied to a silica gel column. Elution with 5% 2M ammonia/methanol in dichloromethane provided the title compound (219 mg, 53%).

Example 12

1-Acetyl-3-[(7-R,S)(8a-R,S)-octahydro-7-indolizinyl]-5-(2-thienyl)indole

1-Acetyl-5-bromo-3-[(7-R,S)(8a-R,S)-octahydro-7-indolizinyl]indole (Example 11, 219 mg, 0.606 mmoles) was mixed with $Pd(PPh_3)_4$ (35 mg, 0.0313 mmol) and 2-(tributylstannyl)thiophene (246.7 mg, 0.66 mmoles) in THF (1 mL) under argon at 80° C. overnight. The product was purified by column chromatography using 2–4% 2M ammonia/methanol in dichloromethane to provide the title compound (120 mg, 54.3%).

Example 13(a)

1-Acetyl-3-[(6-R,S)-1,4-diaza[4.3.0]bicyclonon-4-yl]indole

A solution of 1-acetoxy-3-indolone (300 mg, 1.88 mmol), (6-R,S)-1,4-diaza[4.3.0]bicyclononane (475 mg, 3.77 mmol) and p-toluenesulfonic acid (20 mg) in dry toluene (15 mL) was refluxed through a Dean-Stark trap for 24 hours. The mixture was diluted with methylene chloride, filtered through silica and purified by silica gel chromatography (7.5% methanol in methylene chloride) to give the title compound as a brown oil (140 mg, 26%); $^1$H NMR (CDCl$_3$) δ: 8.46 (br s, 1H), 7.57 (d, 1H), 7.33 (t, 1H), 7.25 (t, 1H), 6.79 (br s, 1H), 5.65 (m, 1H), 3.52 (m, 1H), 3.13 (m, 2H), 2.85 (m, 1H), 2.57 (s, 3H), 2.53–1.44 (m, 8H); $^{13}$C NMR (CDCl$_3$) δ: 168.1, 136.9, 135.5, 126.2, 125.5, 123.1, 119.3, 117.0, 109.4, 62.3, 56.4, 53.5, 51.2, 27.5, 24.2, 21.3;

In a like manner, the following additional compound was prepared:

(b) 1-Acetyl-3-[(6-R,S)-1,4-diaza[4.4.0]bicyclodecan-4-yl]indole: from (6-R,S)-1,4-diaza[4.4.0]bicyclodecane, 27%, brown oil; $^1$H NMR (CDCl$_3$) δ: 8.44 (br s, 1H), 7.54 (d, 1H), 7.32 (t, 1H), 7.23 (t, 1H), 6.74 (br s, 1H), 3.48 (m, 1H), 3.48 (m, 3.32 (m, 1H), 2.80–2.82 (m, 4H), 2.55 (s, 3H), 2.53–1.20 (m, 9H); $^{13}$C NMR (CDCl$_3$) δ: 168.1, 136.7, 135.5, 125.5, 123.1, 119.3, 116.9, 109.2, 60.9, 57.7, 55.6, 54.8, 51.7, 29.7, 25.6, 24.2, 23.9;

Example 14(a)

3-[(6-R,S)-1,4-Diaza[4.3.0]bicyclonon-4-yl]-1H-indole

To a solution of 1-acetyl-3-[(6-R,S)-1,4-diaza[4.3.0]bicyclonon-4-yl]-1H-indole (Example 13a, 122 mg, 0.43 mmol), in methanol (10 mL) was added sodium hydroxide (26 mg, 0.65 mmol) and the resulting solution was refluxed for 15 minutes. The reaction mixture was then poured into ethyl acetate, washed with water and brine and the organic layer dried (Na$_2$SO$_4$), filtered and concentrated to give the title compounds as yellow oil (102 mg, 100%); $^1$H NMR (CDCl$_3$) δ: 8.01, (br s, 1H), 7.65 (d, 1H), 7.28 (d, 7H), 7.17 (t, 1H), 7.07 (t, 1H), 6.72 (d, 1H), 3.65 (m, 1H), 3.50 (m, 1H), 2.90 (m, 4H), 2.65–1.25 (m, 9H); $^{13}$C NMR (CDCl$_3$) δ: 135.7, 132.2, 122.2, 119.1, 118.8, 111.4, 110.6, 62.7, 57.4, 53.5, 52.0, 51.8, 27.5, 21.3;

In a like manner, the following additional compound was prepared:

(b) 3-[(6-R,S)-1,4-Diaza[4.4.0]bicyclodecan-4-yl]-1H-indole: from 1-acetyl-3-[(6-R,S)-1,4-diaza[4.4.0]bicyclodecan-4-yl]-1H-indole (Example 13b), 88%, yellow oil; $^1$H NMR (CDCl$_3$) δ: 7.89 (br s, 1H), 7.64(d, 1H), 7.27 (d, 1H), 7.17 (t, 1H), 7.07 (t, 1H), 6.70 (d, 1H), 3.47 (m, 1H), 3.36 (m, 1H), 2.90 (m, 4H), 2.65–1.24 (m, 9H); $^{13}$C NMR (CDCl$_3$), δ: 135.7, 132.3, 122.1, 119.1, 118.8, 111.4, 110.3, 61.3, 58.8, 55.6, 55.2, 52.6, 29.8, 25.7, 24.0.

(c) 3-[(7-R,S)(8a-R,S)-Octahydro-7-indolizinyl]-5-(2-thienyl)-1H-indole: (76.9 mg, 94%): from 1-acetyl-3-[(7-R,S)(8a-R,S)-octahydro-7-indolizinyl]-5-(2-thienyl)indole (Example 12), (92.5 mg, 0.254 mmoles) and 2M NaOH (0.4 mL) in MeOH (0.6 mL) at room temperature for 16 hrs.

TABLE 1

Summary of Exemplified Compounds of Formulae I and III

| Example # | Structure | Example # | Structure |
|---|---|---|---|
| 3a | 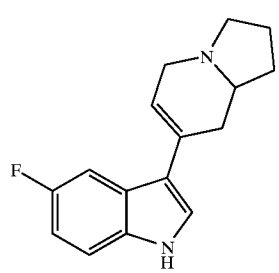 | 3b | 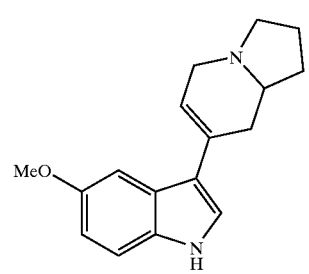 |

TABLE 1-continued
Summary of Exemplified Compounds of Formulae I and III
| Example # | Structure | Example # | Structure |
|---|---|---|---|
| 3c | 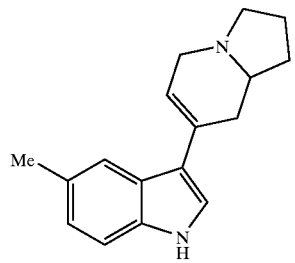 | 3d | 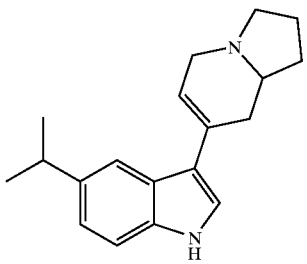 |
| 3e | 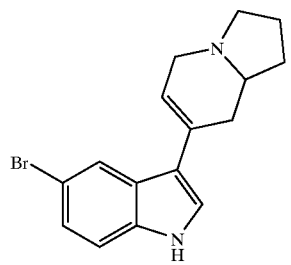 | 3f | 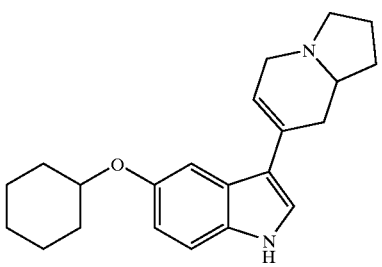 |
| 3g | 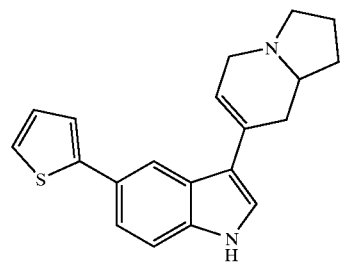 | 3i | 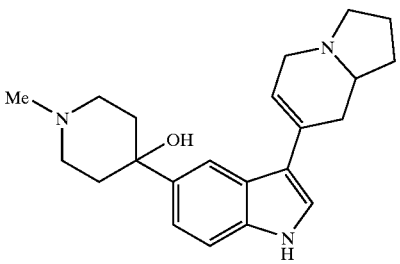 |
| 6 | 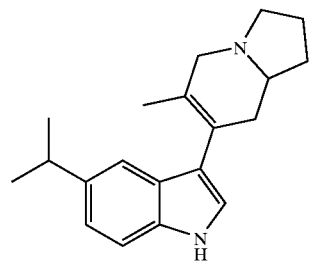 | 7 | 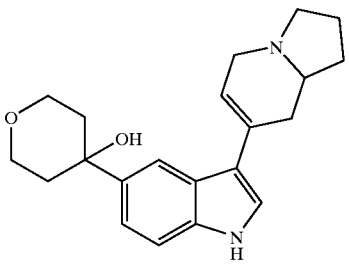 |
| 8a | 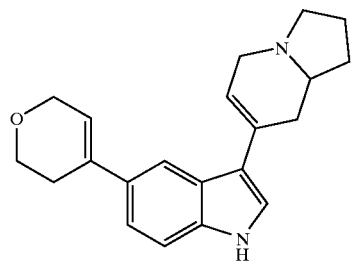 | 8b | 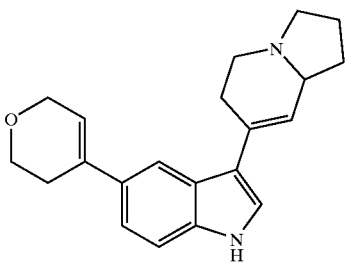 |

TABLE 1-continued
Summary of Exemplified Compounds of Formulae I and III
| Example # | Structure | Example # | Structure |
| --- | --- | --- | --- |
| 8c | 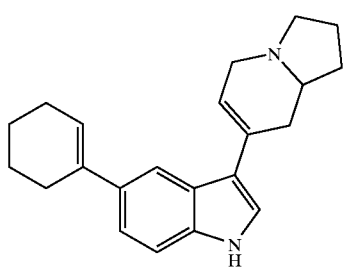 | 8d | 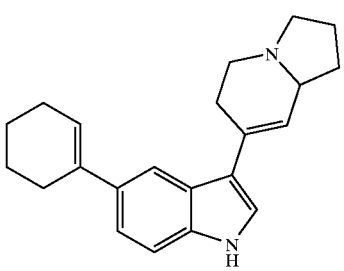 |
| 8e | 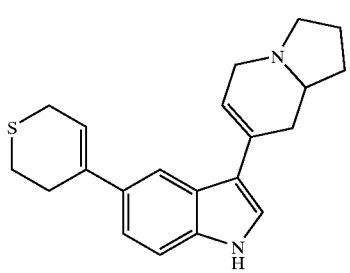 | 8f | 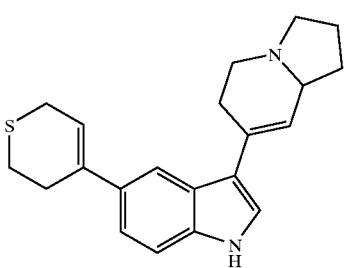 |
| 9a | 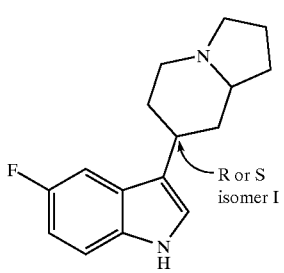 R or S isomer I | 9b | 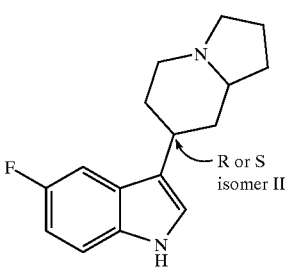 R or S isomer II |
| 9c | 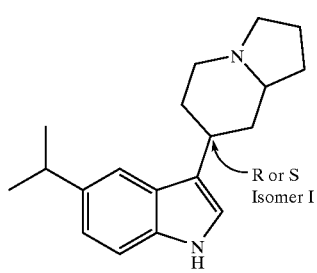 R or S Isomer I | 9d | 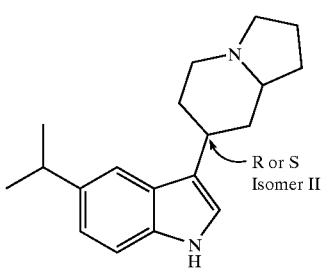 R or S Isomer II |
| 9e | 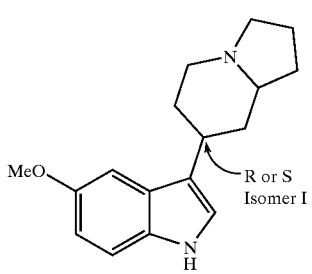 R or S Isomer I | 9f | 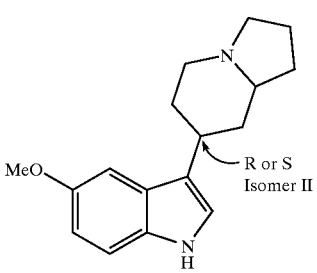 R or S Isomer II |

TABLE 1-continued

Summary of Exemplified Compounds of Formulae I and III

| Example # | Structure | Example # | Structure |
|---|---|---|---|
| 9g | 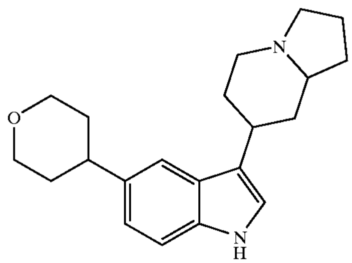 | 10 | 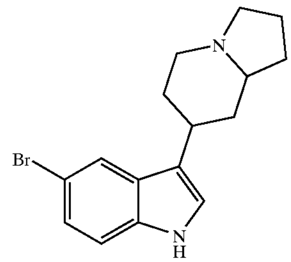 |
| 14a | 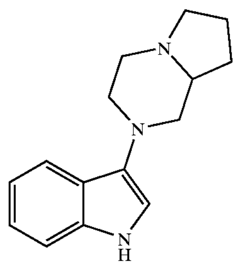 | 14b | 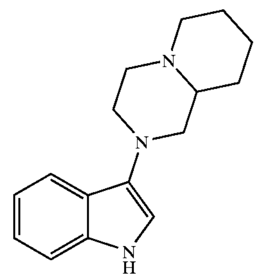 |
| 14c | 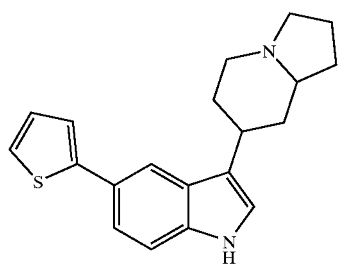 | 3h | 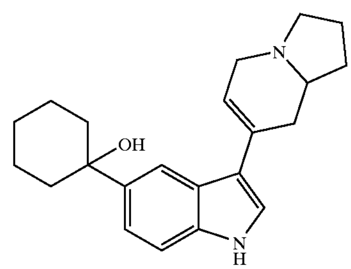 |
| 3j | 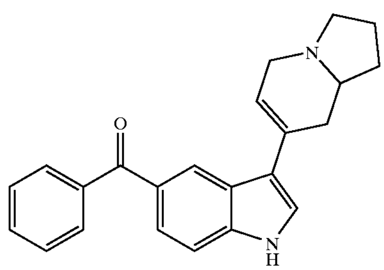 | 9h | R or S, Isomer I |
| 9i | R or S, Isomer II | | |

Example 15

General Procedure for Salt Formation

Hydrochloric acid (for compounds of Formulae I and III where Z=C): acid (4 mol. equiv., 1M in diethyl ether) is added to a solution of the substrate (1 mol. equiv.) in dichloromethane (approx. 0.1 M solution) and the mixture is stirred for 20 min. The solvent and excess acid are removed in vacuo and the crude product is recrystallized from methanol-ether.

Other salts: The appropriate acid (2 mol. equiv. solid acids) are added to a solution of the substrate (1 mol. equiv.) in methanol (0.14 M solution) and the mixture is stirred overnight. The solvent is removed in vacuo and the crude product is purified.

Example 16

Comparison of the Binding Affinities

Selected compounds of the previous examples, as well as reference compounds were evaluated for binding affinity using cell types receptive specifically to $5\text{-HT}_{1D}$ and $5\text{-HT}_{1B}$ ligands. The assay protocol generally entailed the incubation of membranes prepared from cells expressing the $5\text{-HT}_{1D}$ or $5\text{-HT}_{1B}$ subtype of 5-HT receptors with $^3$H-serotonin (1 nM for $5\text{-HT}_{1D}$ and 2.5 nM for $5\text{-HT}_{1B}$). Specific concentrations of the test compound were incubated with the radioligand and the membrane homogenates prepared from the recombinant cells. After a 60 minute incubation at 22° C., the incubation was terminated by vacuum filtration. The filters were washed with buffer and counted for radioactivity using liquid scintillation spectroscopy. The affinity of the test compound for the $5\text{-HT}_{1D}$ receptor is expressed as the amount (in percent) of binding of the radioligand that is inhibited in the presence of 100 nM of test compound. A greater percent inhibition indicates greater affinity for the $5\text{-HT}_{1D}$ receptor. Selected compounds of the invention showed a percent inhibition of greater than 50% at the $5\text{-HT}_{1D}$ receptor. Specific compounds of the invention, for example, those of examples 3b, 3c, 3d, 3e, 3f, 3g, 3h, 6, 7, 8a, 8b, 8c, 8d, 8e, 8f, 9c, 9d, 9d, 9g and 14c showed a percent inhibition of greater than 75% at the $5\text{-HT}_{1D}$ receptor. More specific compounds of the invention, for example, those of examples 3d, 3e, 3g, 7, 8a, 8b, 8c, 8e, 8f, 9c and 9d showed a percent inhibition of greater than 90% at the $5\text{-HT}_{1D}$ receptor. In terms of selectivity, specific compounds of the invention, for example compounds of examples 3b, 3c, 3d, 3h, 6, 7, 8c, 8e, 9c, 9d and 14c, having a percent inhibition of greater than 75% at the $5\text{-HT}_{1D}$ receptor, also had a percent inhibition of less than 50% at the $5\text{-HT}_{1B}$ receptor. More specific compounds, for example those of examples 3c, 3d, 6, 9d and 14c, showed a percent inhibition of greater than 75% at the $5\text{-HT}_{1D}$ receptor and a percent inhibition of less 40% at the $5\text{-HT}_{1B}$ receptor.

Example 17

Functional Assays

The $5\text{HT}_{1D}$ and $5\text{HT}_{1B}$ receptor subtypes respond to serotonin and other agonists by reducing adenyl cyclase mediated production of cyclic AMP. Particular test compounds were assayed for their ability to inhibit adenyl cyclase activity using the procedure described below. Forskolin was used to elevate the basal adenyl cyclase activity.

Compounds acting as antagonists at the $5\text{HT}_{1D}$ and $5\text{HT}_{1B}$ receptor subtypes will antagonize the agonist effect of serotonin and thus, will block the serotonin-induced inhibition of forskolin-stimulated adenyl cyclase activity. CHO Pro 5 cells stably expressing either the human $5\text{HT}_{1D}$ or human $5\text{HT}_{1B}$ receptors were plated in 6 well plates in DMEM (Dulbecco's Modified Eagle Medium)/F12 (Nutrient Mixture F12—Ham) media with 10% FCS (fetal calf serum) and G418 (Geneticen Disulfate, 500 ug/ml), and incubated at 37° C. in a $CO_2$ incubator. The cells were allowed to grow to about 70% confluence before use in the assay.

The culture media of each well was removed, and the wells were washed once with serum free media. Then 2 ml of SFM+IBMX medium (SFM with 0.5 mM IBMX, 3-isobutyl-1-methylxanthine, 0.1% ascorbic acid and 10 mM pargyline) was added to each well and the wells were incubated at 37° C. for 10 min. Following incubation, the SFM+IBMX media was removed from each well and fresh SFM+IBMX media was added to the wells separately with one of a) forskolin (10 mM final concentration); b) serotonin and forskolin (both 10 mM final concentration); c) test compound (100 nM and 10 $\mu$M) and forskolin (10 mM final concentration) (to test for agonist activity); and d) test compound (100 nM and 10 $\mu$M) along with serotonin and forskolin (both 10 mM final concentration) (to test for antagonist activity). Basal adenyl cyclase activity was determined from wells with only SFM+IBMX media added.

The cells were then incubated at 37° C. for 30 minutes in a $CO_2$ incubator. Following incubation, the media were removed from each well. The wells were washed once with 1 ml of PBS (phosphate buffered saline). Each well was then treated with 1 mL cold 95% ethanol:5mM EDTA (2:1) at 4° C. for 1 hour. The cells from each well were then scraped and transferred into individual Eppendorf tubes. The tubes were centrifuged for 5 minutes at 4° C., and the supernatants were transferred to new Eppendorf tubes. The pellets were discarded and the supernatants were stored at 4° C. until assayed for cAMP concentration. cAMP content for each extract was determined in duplicate by EIA (enzyme-immunoassay) using the Amersham Biotrak cAMP EIA kit (Amersham RPN 225).

Total inhibition ($I_o$) of forskolin-stimulated adenyl cyclase activity by serotonin was determined as the difference in concentration of cAMP in the forskolin-treated cells ($C_f$) and serotonin-forskolin treated cells ($C_d$).

$$I_o = C_f - C_d$$

Likewise, inhibition of forskolin-stimulated adenyl cyclase activity by an agonist test compound was determined as the difference in concentration of cAMP in the forskolin-treated cells and test compound-forskolin treated cells. Agonist activity is expressed as %forskolin response.

Net inhibition (I) of forskolin-stimulated adenyl cyclase activity by serotonin in the presence of an antagonist was determined as the difference in concentration of cAMP in the forskolin-treated cells ($C_f$) and cAMP concentrations in test compound, serotonin and forskolin-treated cells (C).

$$I = C_f - C$$

The ability of the test compounds to reverse the serotonin inhibition of forskolin-stimulated adenyl cyclase activity (% reversal, %R) was determined by the formula:

$$\%R = (1 - I/I_o) \times 100$$

The compounds of examples 3d and 14c caused a decrease in the forskolin stimulated production of cAMP in CHO cells stably expressing the $5\text{-HT}_{1D}$ receptor, at concentrations of 100 nM and 10 $\mu$M, and therefore acts as an agonist at this receptor.

Example 18

Pharmaceutical Examples

Tablets

These may be prepared by the normal methods such as wet granulation or direct compression.

| A. Direct Compression | |
|---|---|
| | mg/tablet |
| Active ingredient | 10.0 |
| Microcrystalline Cellulose USP | 188.5 |
| Magnesium Stearate BP | 1.5 |
| Compression weight | 200.0 |

The active ingredient is sieved through a suitable sieve, blended with the excipients and compressed using 7 mm diameter punches. Tablets of other strengths may be prepared by altering the compression weight and using punches to suit.

| B. Wet Granulation | |
|---|---|
| | mg/tablet |
| Active ingredient | 10.0 |
| Lactose BP | 143.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

| C. For Buccal Administration | |
|---|---|
| | mg/tablet |
| Active ingredient | 10.0 |
| Lactose BP | 86.8 |
| Sucrose BP | 86.7 |
| Hydroxypropyl methylcellulose | 15.0 |
| Magnesium Stearate BP | 1.5 |
| Compression weight | 200.0 |

The active ingredient is sieved through a suitable sieve and blended with the lactose, sucrose and hydroxypropylmethylcellulose. Suitable volumes of purified water are added and the powders are granulated. After drying, the granules are screened and blended with the magnesium stearate. The granules are then compressed into tablets using suitable punches.

The tablets may be film-coated with suitable film-forming materials, such as hydroxypropyl methylcellulose, using standard techniques. Alternatively the tablets may be sugar coated.

| Capsules | |
|---|---|
| | mg/capsule |
| Active ingredient | 10.0 |
| *Starch 1500 | 89.0 |
| Magnesium Stearate BP | 1.0 |
| Fill Weight | 100.0 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| Syrup | |
|---|---|
| | mg/5 ml dose |
| Active ingredient | 10.0 |
| Sucrose BP | 2750.0 |
| Glycerine BP | 500.0 |
| Buffer | as required |
| Flavour | as required |
| Colour | as required |
| Preservative | as required |
| Distilled water to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup produced is clarified by filtration.

| Suppositories | |
|---|---|
| Active ingredient | 10.0 mg |
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

| Injection for Intravenous Administration | |
|---|---|
| | % w/v |
| Active ingredient | 0.2 |
| Sodium Chloride BP | as required |
| Water for Injection BP to | 100.00 |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilized by heating in an autoclave using one of the acceptable cycles. Alternatively the solution may be sterilized by filtration and filled into sterile ampoules under aseptic conditions. The solution may be packed under an inert atmosphere of nitrogen or other suitable gas. Inhalation Cartridges

| Inhalation Cartridges | |
|---|---|
| | mg/cartridge |
| Active ingredient micronised | 1.0 |
| Lactose BP | 39.0 |

The active ingredient is micronised (Microniser is a Registered Trade Mark) in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler (Registered Trade Mark).

| Metered Dose Pressurized Aerosol | | |
|---|---|---|
| | mg/metered dose | per can |
| Active ingredient micronised | 0.500 | 120.0 mg |
| Oleic Acid BP | 0.050 | 12.0 mg |
| Trichlorofluoromethane BP | 22.250 | 5.34 mg |
| Dichlorodifluoromethane BP | 62.2 | 14.92 g |

The active ingredient is micronised in a fluid energy mill to a fine particle size range. The oleic acid is mixed with the trichlorofluoromethane at a temperature of 10–15° C. and the pulverized drug is mixed into the solution with a high shear mixer. The suspension is metered into aluminum aerosol cans and suitable metering valves, delivering a metered amount of 85 mg of suspension, are crimped onto the cans and the dichlorodifluoromethane is pressure filled into the cans through the valves.

We claim:

1. A compound according to Formula III and a salt, solvate or hydrate thereof:

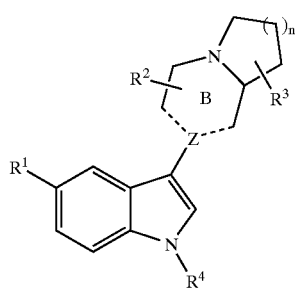

wherein:

$R^1$ is a group of Formula II:

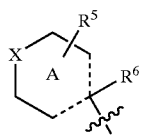

X is selected from the group consisting of O, S, SO, $SO_2$, $NR^{10}$ and $CR^{11}R^{12}$;

- - - - -, in ring A and ring B, represents a single or double bond provided that only one double bond is present in a ring at a time;

$R^2$ is selected from the group consisting of H, OH, $C_{1-6}$alkyl and $C_{1-6}$alkoxy;

$R^3$ is selected from the group consisting of H, OH, $C_{1-6}$alkyl, $C_{1-6}$alkoxy, $C_{1-6}$alkylthio and optionally substituted benzyloxy;

$R^4$ is selected from the group consisting of H and $C_{1-4}$alkyl;

$R^5$ is selected from the group consisting of H, OH, $C_{1-6}$alkyl and $C_{1-6}$alkoxy;

$R^6$ is selected from the group consisting of H, OH, $C_{1-6}$alkoxy or null, provided that when $R^6$ is selected from the group consisting of H, OH and $C_{1-6}$ alkoxy, - - - - - represents a single bond in ring A and when $R^6$ is null, - - - - - represents a double bond in ring A;

$R^{10}$ is selected from the group consisting of H, $C_{1-6}$alkyl, optionally substituted benzyl, $C(O)NHR^{13}$, $SO_2NHR^{13}$ and $C(S)NHR^{13}$;

one of $R^{11}$ and $R^{12}$ is selected from the group consisting of H, $C_{1-6}$alkyl and optionally substituted benzyl and the other is H;

$R^{13}$ is selected from the group consisting of H, $C_{1-6}$alkyl, optionally substituted phenyl, optionally substituted benzyl and optionally substituted naphthyl;

n is selected from the group consisting of an integer of from 1–3;

Z is selected from the group consisting of C and N, provided that when Z is N, - - - - - represents a single bond in ring B.

2. A compound according to claim 1, wherein X is selected from O, S and $CH_2$.

3. A compound according to claim 1, wherein $R^5$ is H.

4. A compound according to claim 1, wherein $R^6$ is null and - - - - - represents a double bond.

5. A compound according to claim 1, wherein $R^6$ is selected from H and OH and - - - - - represents a single bond.

6. A compound according to claim 1, wherein $R^4$ is H.

7. A compound according to claim 1, wherein $R^2$ is selected from H and methyl and $R^3$ is H.

8. A compound according to claim 7, wherein n is selected from 1 and 2.

9. A compound according to claim 8, wherein Z is C.

10. A compound according to claim 9, wherein n is 1 and - - - - - represents a double bond in the 6,7-position of the indolizine ring.

11. A compound according to claim 1, selected from:
1-{[3-(8a-R,S)-1,2,3,5,8,8a-Hexahydro-7-indolizinyl]-1H-indol-5-yl}-N-methyl-4-azacyclohexanol;

4-{[3-(8a-R,S)-1,2,3,5,8,8a-Hexahydro-7-indolizinyl]-1H-indol-5-yl}tetrahydro-2H-pyran-4-ol;

1-{[3-(8a-R,S)-1,2,3,5,8,8a-Hexahydro-7-indolizinyl]-1H-indol-5-yl}cyclohexanol;

5-(5,6-Dihydro-2H-pyran-4-yl)-3-[(8a-R,S)-1,2,3,5,8,8a-hexahydro-7-indolizinyl]-1H-indole;

5-(5,6-Dihydro-2H-pyran-4-yl)-3-[(8a-R,S)-1,2,3,5,6,8a-hexahydro-7-indolizinyl]-1H-indole;

5-(Tetrahydropyran-4-yl)-[(7-R,S)(8a-R,S)-octahydro-7-indolizinyl]-1H-indole;

5-(Cyclohexen-1-yl)-3-[(8a-R,S)-1,2,3,5,8,8a-hexahydro-7-indolizinyl]-1H-indole;

5-(Cyclohexen-1-yl)-3-[(8a-R,S)-1,2,3,5,6,8a-hexahydro-7-indolizinyl]-1H-indole;

5-(5,6-Dihydro-2H-thiopyran-4-yl)-3-[(8a-R,S)-1,2,3,5,8,8a-hexahydro-7-indolizinyl]-1H-indole; and 5-(5,6-Dihydro-2H-thiopyran-4-yl)-3-[(8a-R,S)-1,2,3,5,6,8a-hexahydro-7-indolizinyl]-1H-indole.

12. A compound according to Formula III,

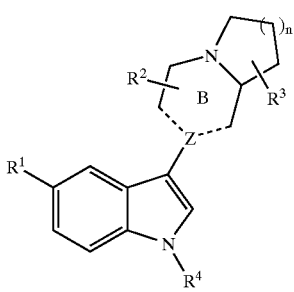

wherein

R$^1$ is selected from the group consisting of optionally substituted phenyl, optionally substituted furanyl, optionally substituted thienyl and optionally substituted phenyloxy;

R$^2$ is selected from the group consisting of H, OH, C$_{1-6}$alkyl, and C$_{1-6}$alkoxy;

R$^3$ is selected from the group consisting of H, OH, C$_{1-6}$alkyl, C$_{1-6}$alkoxy, C$_{1-6}$alkythio and optionally substituted benzyloxy;

R$^4$ is selected from the group consisting of H and C$_{1-4}$alkyl;

n is selected from the groups consisting of an integer of from 1–3; and

Z is selected from the group consisting of C and N, provided that when Z is N, - - - - - represents a single bond in ring B.

13. A compound according to claim 12, wherein R$^1$ is selected from the group consisting of optionally substituted furanyl and optionally substituted thienyl.

14. A pharmaceutical composition, comprising a pharmaceutically acceptable carrier and, in an amount effective to stimulate a 5-HT$_{1D}$ receptor, a compound according to Formula I:

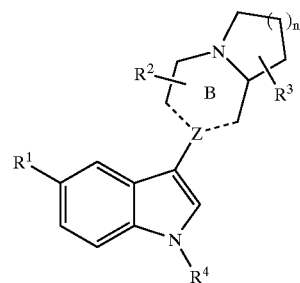

wherein:

R$^1$ is selected from the group consisting of a group of Formula II:

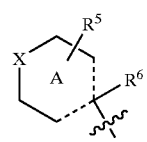

C$_{1-6}$alkyl, C$_{1-6}$alkoxy, C$_{2-6}$alkenyl, C$_{2-6}$alkynyl, C$_{3-7}$cycloalkyl, C$_{4-7}$cycloalkenyl, C$_{3-7}$cycloalkoxy, C$_{3-7}$cycloalkylthio, halo-substituted-C$_{1-6}$alkyl, C$_{2-7}$alkanoyloxy, cyano, optionally substituted phenyl, optionally substituted furanyl, optionally substituted thienyl, optionally substituted phenyloxy, CH$_2$SO$_2$NR$^7$R$^8$, OC(O)R$^9$, NR$^{14}$R$^{15}$, SO$_2$NR$^{14}$R$^{15}$, CO$_2$R$^{16}$; NHC(NR$^{18}$)R$^{17}$, C(NR$^{19}$)NR$^{20}$R$^{21}$, SCF$_3$, SO$_2$CF$_3$, CF$_3$ and CF$_3$O;

X is selected from the group consisting of O, S, SO, SO$_2$, NR$^{10}$ and CR$^{11}$R$^{12}$;

- - - - -, in ring A and ring B, represents a single or double bond provided that only one double bond is present in a ring at a time;

R$^2$ is selected from the group consisting of H, OH, C$_{1-6}$alkyl and C$_{1-6}$alkoxy;

R$^3$ is selected from the group consisting of H, OH, C$_{1-6}$alkyl, C$_{1-6}$alkoxy, C$_{1-6}$alkylthio and optionally substituted benzyloxy;

R$^4$ is selected from the group consisting of H and C$_{1-4}$alkyl;

R$^5$ is selected from the group consisting of H, OH, C$_{1-6}$alkyl and C$_{1-6}$alkoxy;

R$^6$ is selected from the group consisting of H, OH, C$_{1-6}$alkoxy or null, provided that when R$^6$ is selected from the group consisting of H, OH and C$_{1-6}$ alkoxy, - - - - - represents a single bond in ring A and when R$^6$ is null, - - - - - represents a double bond in ring A;

R$^7$ and R$^8$ are independently selected from the group consisting of H and C$_{1-6}$alkyl;

R$^9$ is selected from the group consisting of optionally substituted phenyl, optionally substituted pyridyl, optionally substituted thienyl, optionally substituted furanyl and optionally substituted naphthyl;

R$^{10}$ is selected from the group consisting of H, C$_{1-6}$alkyl, optionally substituted benzyl, C(O)NHR$^{13}$, SO$_2$NHR$^{13}$ and C(S)NHR$^{13}$;

one of R$^{11}$ and R$^{12}$ is selected from the group consisting of H, C$_{1-6}$alkyl and optionally substituted benzyl, and the other is H;

$R^{13}$ is selected from the group consisting of H, $C_{1-6}$alkyl, optionally substituted phenyl, optionally substituted benzyl and optionally substituted naphthyl;

$R^{14}$ and $R^{15}$ are independently selected from the group consisting of H, $C_{1-6}$alkyl and phenyl, or $R^{14}$ and $R^{15}$ may form an alkylene bridge, —$(CH_2)_a$—, where a=3–6, to form, together with the nitrogen to which they are attached, a 4- to 7-membered ring; with the proviso that both $R^{14}$ and $R^{15}$ cannot be H;

$R^{16}$ is selected from the group consisting of H, $C_{1-6}$alkyl and phenyl;

$R^{17}$ is selected from the group consisting of H, $C_{1-6}$alkyl, $C_{1-8}$alkoxy, phenyl, phenoxy, $NH_2$, alkylamino, dialkylamino, benzyl and benzyloxy;

$R^{18}$ is selected from the group consisting of H and $C_{1-6}$alkyl;

$R^{19}$ is selected from the group consisting of H and $C_{1-6}$alkyl;

$R^{20}$ and $R^{21}$ are independently selected from the group consisting of H and $C_{1-6}$alkyl or one of $R^{20}$ and $R^{21}$, together with $R^{19}$, forms an alkylene bridge, —$(CH_2)_c$—, where c=2 or 3, connecting the nitrogen atoms to which they are attached;

n is selected from the group consisting of an integer of from 1–3; and

Z is selected from the group consisting of C and N, provided that when Z is N, - - - - - represents a single bond in ring B.

15. A pharmaceutical composition according to claim 14, wherein said compound is one in which $R^1$ is selected from a group of Formula II, $C_{1-6}$alkyl, unsubstituted thienyl and unsubstituted furanyl.

16. A pharmaceutical composition according to claim 15, wherein said compound is one in which $R^1$ is selected from methyl, isopropyl, tetrahydro-2H-pyran-4-ol, cyclohexen-1-yl and 5,6-dihydro-2H-thiopyran-4-yl.

17. A pharmaceutical composition according to claim 14, wherein said compound is selected from:

5-methoxy-3-[(8a-R,S)-1,2,3,5,8,8a-hexahydro-7-indolizinyl]-1H-indole;

5-methyl-3-[(8a-R,S)-1,2,3,5,8,8a-hexahydro-7-indolizinyl]-1H-indole;

5-isopropyl-3-[(8a-R,S)-1,2,3,5,8,8a-hexahydro-7-indolizinyl]-1H-indole;

5-cyclohexyloxy-3-[(8a-R,S)-1,2,3,5,8,8a-hexahydro-7-indolizinyl]-1H-indole;

5-(2-thienyl)-3-[(8a-R,S)-1,2,3,5,8,8a-hexahydro-7-indolizinyl]-1H-indole;

5-isopropyl-3-[(8a, R,S)-6-methy-1,2,3,5,8,8a-hexahydro-7-indolizinyl]-1H-indole;

1-{[3-(8a-R,S)-1,2,3,5,8,8a-hexahydro-7-indolizinyl]-1H-indole-5-yl}cyclohexanol;

1-{[3-(8a-R,S)-1,2,3,5,8,8a-hexahydro-7-indolizinyl]-1H-indole-5-yl}-N-methyl-4-azacyclohexanol;

4-{[3-(8a-R,S)-1,2,3,5,8,8a-hexahydro-7-indolizinyl]-1H-indole-5-yl}tetrahydro-2H-pyran-4-ol;

5-(5,6-dihydro-2H-pyran-4-yl)-3-[(8a-R,S)-1,2,3,5,8,8a-hexahydro-7-indolizinyl]-1H-indole;

5-(5,6-dihydro-2H-pyran-4-yl)-3-[(8a-R,S)-1,2,3,5,6,8a-hexahydro-7-indolizinyl]-1H-indole;

5-isopropyl-3-[(7R or 7S)(8a-R,S)-octahydro-7-indolizinyl]-1H-indole, Isomer I;

5-isopropyl-3-[(7R or 7S)(8a-R,S)-octahydro-7-indolizinyl]-1H-indole, Isomer II;

5-methoxy-[(7R or 7S)(8a-R,S)-octahydro-7-indolizinyl]-1H-indole, Isomer I;

5-methoxy-3-[(7R or 7S)(8a-R,S)-octahydro-7-indolizinyl]-1H-indole, Isomer II;

5-(tetrahydropyran-4-yl)-[(7-R,S)(8a-R,S)-octahydro-7-indolizinyl]-1H-indole;

5-(cyclohexen-1-yl)-3-[(8a-R,S)-1,2,3,5,8,8a-hexahydro-7-indolizinyl]-1H-indole;

5-(cyclohexen-1-yl)-3-[(8a-R,S)-1,2,3,5,6,8a-hexahydro-7-indolizinyl]-1H-indole;

5-(5,6-dihydro-2H-thiopyran-4-yl)-3-[(8a-R,S)-1,2,3,5,8,8a-hexahydro-7-indolizinyl]-1H indole;

5-(5,6-dihydro-2H-thiopyran-4-yl)-3-[(8a-R,S)-1,2,3,5,6,8a-hexahydro-7-indolizinyl]-1H-indole;

3-[(7-R,S)(8a-R,S)-octahydro-7-indolizinyl]-5-(2-thienyl)-1H-indole;

3-(1,2,3,5,8,8a-hexahydro-7-indolizinyl)-5-trifluoromethoxy-1H-indole;

3-(1,2,3,5,8,8a-hexahydro-7-indolizinyl)-5-trifluoromethyl-1H-indole;

3-(octahydro-7-indolizinyl)-5-trifluoromethoxy-1H-indole, Isomer I;

3-(octahydro-7-indolizinyl)-5-trifluoromethoxy-1H-indole, Isomer II;

3-(1,2,3,5,8,8a-hexahydro-7-indolizinyl)-5-(1-hydroxy-cyclohexyl)-1H-indole;

5-(1-hydroxy-cyclohexyl)-3-(octahydro-7-indolizinyl)-1H-indole;

5-cyclohexenyl-3-(octahydro-7-indolizinyl)-1H-indole, Isomer I; and 5-cyclohexenyl-3-(octahydro-7-indolizinyl)-1H-indole, Isomer II.

18. A pharmaceutical composition according to claim 14, wherein said compound is selected from:

5-Methyl-3-[(8a-R,S)-1,2,3,5,8,8a-hexahydro-7-indolizinyl]-1H-indole;

5-Isopropyl-3-[(8a-R,S)-1,2,3,5,8,8a-hexahydro-7-indolizinyl]-1H-indole;

5-Isopropyl-3-[(8a,R,S)-6-methyl-1,2,3,5,8,8a-hexahydro-7-indolizinyl]-1H-indole;

5-Isopropyl-3-[(7R or 7S)(8a-R,S)-octahydro-7-indolizinyl]-1H-indole, Isomer II; and 3-[(7-R,S)(8a-R,S)-Octahydro-7-indolizinyl]-5-(2-thienyl)-1H-indole.

19. A method for treating a patient having migraine, comprising the step of administering to the patient a pharmaceutical composition as defined in claim 14.

* * * * *